United States Patent [19]

Tanikawa et al.

[11] Patent Number: 4,978,665

[45] Date of Patent: Dec. 18, 1990

[54] 3(2H)PYRIDAZINONE, AND ANTAGONISTIC AGENT AGAINST SRS-A CONTAINING IT

[75] Inventors: Keizo Tanikawa; Ryozo Sakoda, both of Funabashi; Ken-ichi Shikada; Sakuya Tanaka, both of Shiraoka, all of Japan

[73] Assignee: Nissan Chemical Industries Ltd., Tokyo, Japan

[21] Appl. No.: 144,173

[22] Filed: Jan. 15, 1988

[30] Foreign Application Priority Data

Jan. 20, 1987 [JP] Japan .................. 62-10231

[51] Int. Cl.$^5$ ................ C07D 237/22; A61K 31/50
[52] U.S. Cl. .............................. 514/247; 544/239; 544/241
[58] Field of Search ............. 514/247; 544/239, 241, 544/240

[56] References Cited

U.S. PATENT DOCUMENTS 4,296,120 10/1981 Kadin .
4,892,947 1/1990 Mutsukado et al. ............. 544/241

FOREIGN PATENT DOCUMENTS 784639 5/1968 Canada .
186817 9/1985 European Pat. Off. .
193853 2/1986 European Pat. Off. .
1441438 11/1964 France .
1413955 9/1965 France .

Primary Examiner—Nicholas S. Rizzo
Attorney, Agent, or Firm—Oblon, Spivak, McClelland, Maier & Neustadt

[57] ABSTRACT

A 3(2H)pyridazinone of the formula:

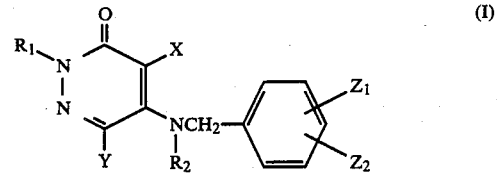

(I)

wherein $R_1$ is hydrogen, 2-propenyl or straight chained or branched $C_1$–$C_4$ alkyl; $R_2$ is hydrogen or $C_1$–$C_3$ alkyl; X is chlorine or bromine; Y is hydrogen, nitro, -$NHR_3$ wherein $R_3$ is hydrogen or straight chained or branched $C_1$–$C_4$ alkyl, -$AR_4$ wherein A is oxygen or sulfur and $R_4$ is hydrogen, straight chained or branched $C_1$–$C_6$ alkyl, $C_3$–$C_6$ alkenyl having one double bond, $C_3$–$C_6$ alkynyl having one triple bond, phenyl or

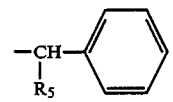

wherein $R_5$ is hydrogen or $C_1$–$C_4$ alkyl, or halogen; $Z_1$ is hydrogen, $C_1$–$C_4$ alkyl, -$OR_6$ wherein $R_6$ is hydrogen, straight chained or branched $C_1$–$C_8$ alkyl or

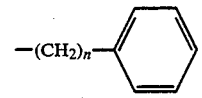

wherein n is an integer of from 1 to 4, -$N(R_7)_2$ wherein $R_7$ is $C_1$–$C_4$ alkyl, or halogen; $Z_2$ is $C_1$–$C_4$ alkyl, -$OR_6$ wherein $R_6$ is as defined above, -$N(R_7)_2$ wherein $R_7$ is as defined above, or halogen, provided that when $R_1$ is straight chained or branched $C_2$–$C_4$ alkyl, Y is not hydrogen and when $R_1$ is hydrogen, methyl or 2-propenyl, Y and $R_2$ are not simultaneously hydrogen, or a pharmaceutically acceptable salt thereof.

29 Claims, No Drawings

3(2H)PYRIDAZINONE, AND ANTAGONISTIC AGENT AGAINST SRS-A CONTAINING IT

The present invention relates to a novel 3(2H)pridazinone which exhibits antagonism against slow reacting substance of anaphylaxis (SRS-A), a process for its preparation and a pharmaceutical composition containing it.

SRS-A is a chemical mediator released together with histamine, etc. by an allergic reaction and has pharmacological activity to contract bronchial smooth muscle strongly and continuously. It has long been known from such a phenomenal aspect. It was found in 1979 that SRS-A itself is a mixture of leukotriene $C_4$, $D_4$ and $E_4$ (generally called peptide leukotriene). Extensive researches have been conducted on SRS-A for its relationship with acosmia. As a result, the relationship of SRS-A with immediate type allergic diseases such as bronchial asthma, allergic rhinitics, urticaria and hay fever, has become clear. Further, the relationship of SRS-A with various inflammatory diseases, ischemic heart diseases, etc., has been suggested. Therefore, a compound which exhibits antagonism against SRS-A, is expected to be useful as a prophylactic or therapeutic drug against the affections caused by either leukotriene $C_4$, $D_4$ or $E_4$, or by a mixture thereof.

As the antagonists against SRS-A, FPL-55712 and its structural analogues as well as some medicinal substances, have been reported (Agents and Actions, vol 9, p. 133–140 (1979), Annual Reports in Medicinal Chemistry, vol. 20, p. 71–81 (1985) and Agents and Actions, vol. 18, p. 332–341 (1986)) However, no instance of their clinical application has been reported.

Now, the relationship of the compounds of the present invention with compounds disclosed in published references will be described.

Canadian Pat. No. 784,639 (hereinafter referred to as reference (a)) discloses 3(2H)pyridazinone derivatives having hydrogen, $C_1$–$C_8$ alkyl, phenyl or $C_3$–$C_8$ cycloalkyl at 2-position, chlorine or bromine at 4-position and benzylamino at 5-position. However, the reference has no Examples corresponding to the compounds of the present invention, and the application of the compounds disclosed in this reference (a) is restricted to a herbicide, and no mention is made as to their medical use or pharmacological activities.

Chemical Abstract, 62, 2773b, (Bull. Soc. Chim, France, 1964 (9) p 2124–32) (reference (b)) discloses 3(2H)pyridazinones having hydrogen or diethylaminoethyl at 2-position, chlorine at 4-position and benzylamino at 5-position. However, this reference (b) has no Examples corresponding to the compounds of the present invention, and it is silent about medical use or pharmacological activities.

German Patent Application No. 1,670,169 published on Nov, 5, 1970 (reference (c)) discloses 3(2)prydazinones having hydrogen or an aliphatic, cycloaliphatic, araliphatic or aromatic group at 2-position, chlorine or bromine at 4-position and aralkylamino at 5-position. This reference (c) discloses a process for the synthesis of pyridazinones including such compounds, their application to agricultural chemicals, their application as intermediates for medicines or dyestuffs, or their application as intermediates for various compounds. However, no mention is made to their pharmacological activities, and no specific examples are given for such compounds. Further, such compounds are not specifically described.

Angew. Chem. International Edition, vol. 4, p. 292–300 (1965) (reference (d)) discloses 3(2H)pyridazinones having hydrogen at 2-position, chlorine at 4-position and N-methyl-benzylamino at 5-position. However, this reference (d) has no Examples corresponding to the compounds of the present invention, and no mention is made as to medical use or pharmacological activities.

The present inventors have conducted extensive researches with an object to find compounds which exhibit antagonism against SRS-A. They have found that 5-substituted benzylamino-3(2H)pyridazinone derivatives having various functional groups and substitution modes, attain the above object, and have already filed patent applications (Japanese Unexamined Patent Publication No. 267560/1986 (reference (e)) and Japanese Unexamined Patent Publication No. 0751/1986 (reference (f)). However, the compounds disclosed in these references (e) and (f) are restricted to 3(2H)pyridazinones having no substituent at 6-position (hydrogen). Further, reference (f) discloses 5-substituted benzylamino-3(2H)pyridazinone derivatives having hydrogen or 2-propenyl at 2-position. However, the amino at 5-position is secondary amino in all cases, and no compound having tertiary amino is included therein.

The present inventors have then conducted extensive researches on compounds having antagonistic activities against SRS-A, and it has been surprisingly found that 3(2H)pyridazinones of the formula I and their pharmacologically acceptable salts are more excellent in the antagonistic activities against SRS-A, and that they are useful as active ingredients for prophylactic or therapeutic drugs against diseases caused by leukotriene $C_4$, $D_4$ or $E_4$, or by a mixture thereof which is a component of SRS-A. The present invention has been accomplished on the basis of this discovery.

The present invention provides a 3(2H)pyridazinone of the formula:

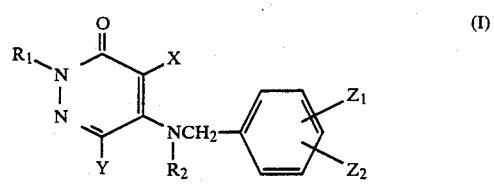

wherein $R_1$ is hydrogen, 2-propenyl or straight chained or branched $C_1$–$C_4$ alkyl; $R_2$ is hydrogen or $C_1$–$C_3$ alkyl; X is chlorine or bromine; Y is hydrogen, nitro, —$NHR_3$ wherein $R_3$ is hydrogen or straight chained or branched $C_1$–$C_4$ alkyl, —$AR_4$ wherein A is oxygen or sulfur and $R_4$ is hydrogen, straight chained or branched $C_1$–$C_6$ alkyl, $C_3$–$C_6$ alkenyl having one double bond, $C_3$–$C_6$ alkynyl having one triple bond, phenyl or

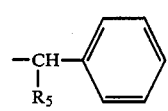

wherein $R_5$ is hydrogen or $C_1$–$C_4$ alkyl, or halogen; $Z_1$ is hydrogen, $C_1$–$C_4$ alkyl, —$OR_6$ wherein $R_6$ is hydrogen, straight chained or branched $C_1$–$C_8$ alkyl or

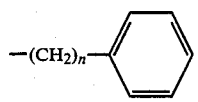

wherein n is an integer of from 1 to 4, —N(R$_7$)$_2$ wherein R$_7$ is C$_1$–C$_4$ alkyl, or halogen; Z$_2$ is C$_1$–C$_4$ alkyl, —OR$_6$ wherein R$_6$ is as defined above, —N(R$_7$)$_2$ wherein R$_7$ is as defined above, or halogen, provided that when R$_1$ is straight chained or branched C$_2$–C$_4$ alkyl, Y is not hydrogen and when R$_1$ is hydrogen, methyl or 2-propenyl, Y and R$_2$ are not simultaneously hydrogen, or a pharmaceutically acceptable salt thereof.

Now, the present invention will be described with reference to the preferred embodiment. Specific examples of substituents R$_1$, R$_2$, X, Y, Z$_1$ and Z$_2$ in the formula I will be described. However, it should be understood that the present invention is by no means restricted to such specific examples. In the following substituents, "n" means normal, "i" means iso, "sec" means secondary and "t" means tertiary.

R$_1$ includes hydrogen, 2-propenyl, methyl, ethyl, n-propyl, i-propyl, n-butyl, i-butyl, sec-butyl and t-butyl. Among them, preferred is hydrogen, ethyl or i-propyl. More preferred is hydrogen.

R$_2$ includes hydrogen, methyl, ethyl and n-propyl. Preferred is hydrogen.

X includes chlorine and bromine.

Y includes hydrogen, nitro, amino, —NHR$_3$ wherein R$_3$ is methyl, ethyl, n-propyl, i-propyl, n-butyl, i-butyl or sec-butyl, —AR$_4$ wherein AR$_4$ is a combination of A being oxygen or sulfur and R$_4$ being hydrogen, methyl, ethyl, n-propyl, i-propyl, n-butyl, i-butyl, sec-butyl, t-butyl, n-pentyl, i-pentyl, sec-pentyl, n-hexyl, i-hexyl, sec-hexyl, 2-propenyl, 2-butenyl, 2-pentenyl, 2-hexenyl, 2-methyl-2-propenyl, 2-ethyl-2-propenyl, 2-n-propyl-2-propenyl, 1-methyl-2-propenyl, 2-ethyl-2-propenyl, 2-propynyl(propargyl), 2-butynyl, 2-pentynyl, 1-methyl-2-propynyl, 2-ethyl-2-propynyl, benzyl, α-methylbenzyl, α-ethylbenzyl, α-n-propylbenzyl or α-n-butylbenzyl), fluorine, chlorine, bromine and iodine. Among them, preferable examples of Y are nitro and —OR$_4$ wherein R$_4$ is the alkyl, alkenyl, alkynyl, benzyl or substituted benzyl as specified above in the definition of AR$_4$.

Z$_1$ includes hydrogen, methyl, ethyl, n-propyl, n-butyl, hydroxyl, methoxy, ethoxy, n-propoxy, i-propoxy, n-butoxy, i-butoxy, n-pentoxy, n-hexyloxy, n-heptyloxy, n-octyloxy, benzyloxy, 2-phenylethoxy, 3-phenylpropoxy, 4-phenylbutoxy, dimethylamino, diethyamino, di-n-propylamino, di-n-butylamino, fluorine, chlorine, bromine and iodine. Z$_2$ includes the same substituents as mentioned for Z$_1$ except that it does not include hydrogen. Among possible combinations of Z$_1$ and Z$_2$, preferred is a combination of the above-mentioned alkyl and/or alkoxy groups such as 3,4-dialkoxy or 3-alkyl-4-alkoxy. A more preferable combination of Z$_1$ and Z$_2$ is 3-alkoxy-4-methoxy or 3-alkyl-4-methoxy.

Among the compounds of the formula I, preferable compounds are represented by the formula IC:

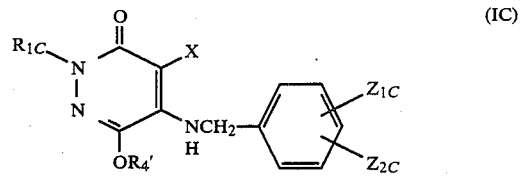

wherein R$_{1C}$ is hydrogen, ethyl or i-propyl; X is chlorine or bromine; R$_4'$ is the same substituent as R$_4$ as defined in the formula I except that it does not include hydrogen; Z$_{1C}$ is hydrogen or —OR$_6$ wherein R$_6$ is straight chained C$_1$–C$_8$ alkyl or

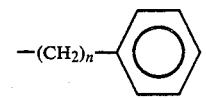

wherein n is an integer of 1 to 4; and Z$_{2C}$ is —OR$_6$ wherein R$_6$ is as defined above.

Among the compounds of the formula IC, particularly preferred are Compound No. 56, 57, 58, 60, 61, 63, 64, 65, 66, 67, 68, 69, 84, 85, 86, 88, 89, 90 and 91 as identified in Table 5.

The compounds of the formula I may have E- and Z-form isomers depending upon the presence of a double bond, and optical isomers or stereoisomers depending upon the presence of 1 to 3 asymmetric carbon. The present invention includes all these isomers and mixtures thereof.

Now, the process for producing the compounds of the present invention will be described. The compounds of the formula I of the present invention can be prepared by the following processes 1 to 5.

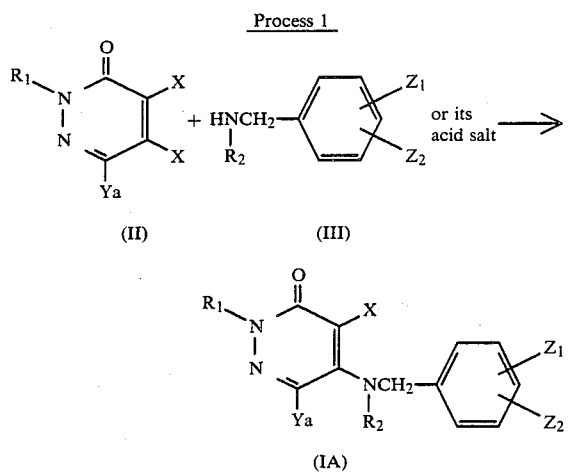

In the above formulas, R$_1$, R$_2$, X, Z$_1$ and Z$_2$ are as defined above with respect to the formula I; Ya is hydrogen, nitro, amino or —OR$_4$ wherein R$_4$ is as defined above with respect to the formula I, or halogen.

Process 1 comprises reacting a 4,5-dihalo-3(2H)pridazinone compound of the formula II with a benzylamine derivative of the formula III or its acid salt in an inert solvent, if necessary in the presence of a dehydrohalogenating agent to obtain a compound of the formula IA, which is a compound of the formula I having Ya at 6-position wherein Ya is as defined above.

In process 1 compound of the formula VA:

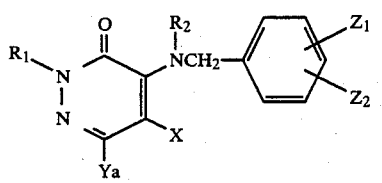

wherein all symbols are as defined above, which is a position isomer of the compound of the formula IA having benzyl amino at 4-position, is formed as a by-product.

The production ratios of the compounds IA and VA depend primarily upon the polarity of the solvent used. Namely, when a solvent of high polarity is used, the production ratio of the compound IA of the present invention tends to be high. Conversely, when a solvent of low polarity such as benzene, toluene or hexane is used, the production ratio of the compound VA tends to be high. Therefore, as a suitable solvent for efficient production of the compound IA of the present invention, an ether solvent such as tetrahydrofuran or 1,4-dioxane, an amide solvent such as formamide, N,N-dimethylformamide, N,N-dimethylacetamide or N-methylpyrrolidone, acetonitrile, dimethylsulfoxide, an alcohol solvent such as methanol, ethanol or propanol, an organic amine solvent such as pyridine or triethylamine, or water, or a solvent mixture thereof, may be mentioned. The desired 5-benzylamino isomer IA can readily be separated and purified from the mixture of the 4- and 5-benzylamino isomers by conventional methods known per se in organic synthesis, such as fractional recrystallization or various silica gel chromatography.

During the reaction, hydrogen chloride or hydrogen bromide is generated. It is usually advantageous to add to the reaction system a dehydrohalogenating agent which traps such a hydrogen halide.

Any dehydrohalogenating agent may be used so long as it does not adversely affect the reaction and is capable of trapping a hydrogen halide. As such a dehydrohalogenating agent, an inorganic base such as potassium carbonate, sodium carbonate, potassium hydrogencarbonate, or sodium hydrogencarbonate, or an organic base such as N,N-dimethylaniline, N,N-diethylaniline, trimethylamine, triethylamine or pyridine, may be mentioned. Otherwise, the benzylamine III starting material itself may be used in an excessive amount as the hydrogen halide trapping agent. This gives preferred results in many cases. The reaction temperature may be within a range of from 10° C. to the boiling point of the solvent used for the reaction.

The molar ratio of the starting materials may optionally be set. However, the benzylamine derivative of the formula III may be used in an amount of from 1 to 10 moles relative to one mole of the 4,5-dihalo-3(2H)pyridazinone derivative of the formula II, and usually, it is enough that from 1.2 to 5 moles thereof is used.

The 4,5-dihalo-3(2H)pyridazinone derivative II as one of the starting materials can be prepared by a conventional process or by an application of a conventional organic reaction as described below. Namely, the compound of the formula IIa or the formula II wherein Ya is hydrogen, can be prepared by the methods disclosed in the above-mentioned references (e) and (f).

Further, the compound of the formula IIb or the formula II wherein Ya is nitro, can be prepared from the compound IIa by the methods disclosed in Japanese Examined Patent Publication Nos. 1299/1967 and 20096/1969 as shown in process 1-(1).

Process 1-(1)

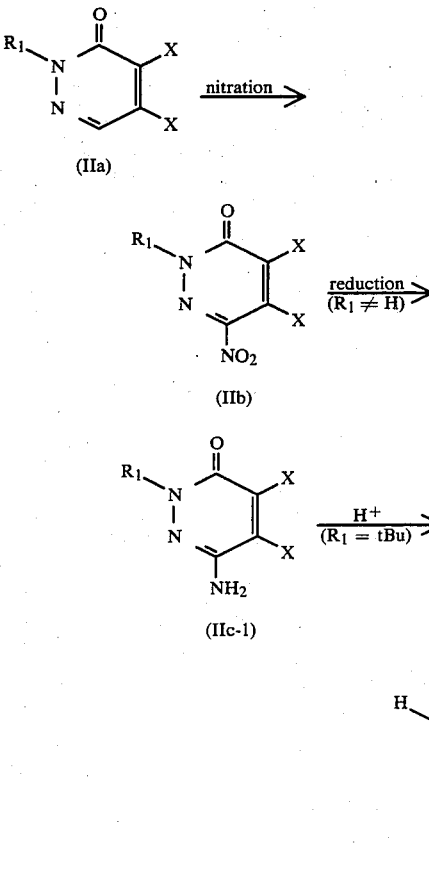

In the above formulas, $R_1$ and X are as defined above with respect to the formula I.

The compounds of the formulas IIc-1 and IIc-2 wherein Ya is amino can be prepared, respectively, by the method disclosed in Japanese Examined Patent Publication No. 5298/1969 or by a method of treating the 6-amino-4,5-dihalo-3(2H)pyridazinone derivative wherein $R_1$ is t-butyl, with a mineral acid such as hydrochloric acid or sulfuric acid or an organic acid such as trifluoroacetic acid or methanesulfonic acid, to remove t-butyl at 2-position.

Further, the compounds of the formulas IId-1 and IId-2 wherein Ya is hydroxyl, and the compound of the formula IId-3 wherein Ya is alkoxy, can easily be prepared by the method as shown in Process 1-(2). Namely, the 6-hydroxy-4,5-dihalopyridazinone derivative can usually be prepared by the ring closure condensation reaction of a hydrazine or its acid salt with a dihalomaleic anhydride. Further, the compound having a substituent at 2-position, can be prepared by employing a process using the compound of the formula IId-2 as the intermediate.

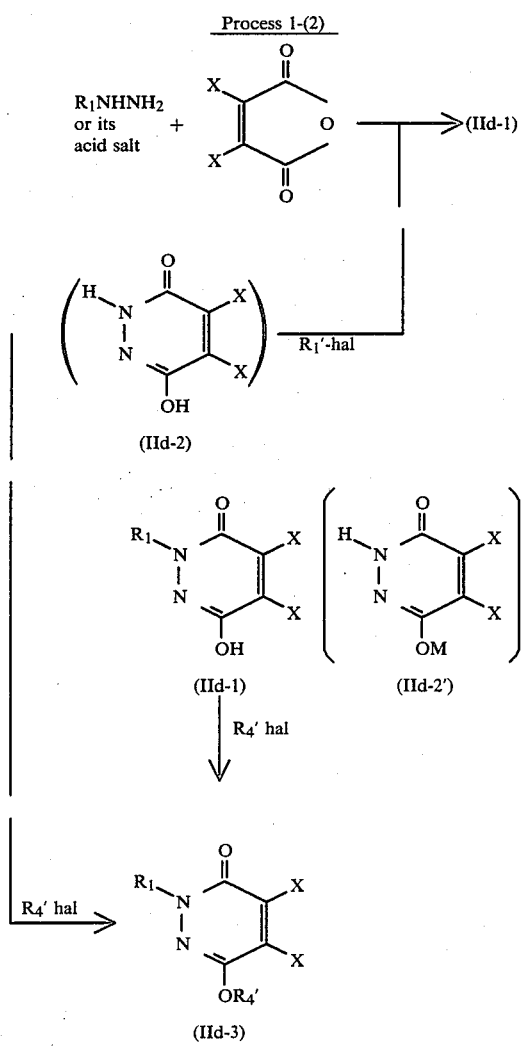

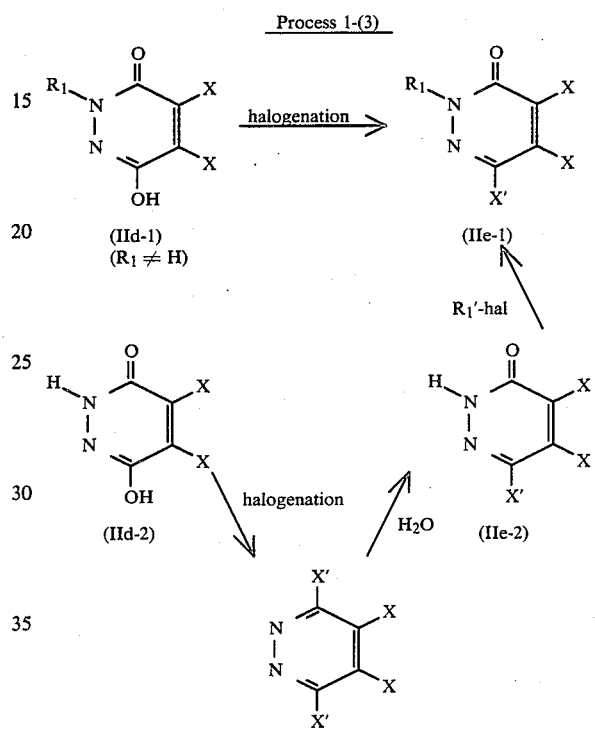

metal salt IId-2' and the isolated alkali metal salt is reacted with $R_4'$-hal in a nonaqueous solvent system.

Further, compounds of the formula IIe-1 and IIe-2, which are compounds of the formula II wherein Ya is a halogen, can be prepared by using or applying the method disclosed in Monatshefte fur Chemie, vol 99, 15 (1968) or Japanese Examined Patent Publication No. 24029/1972.

In the above formulas, $R_1$ and X are as defined above with respect to the formula I, $R_1'$ is straight chained or branched $C_1-C_4$ alkyl or 2-propenyl, $R_4'$ is the same substituent as $R_4$ defined above with respect to the formula I except that it does not include hydrogen, hal is chlorine, bromine or iodine, and M is alkali metal.

With respect to the reaction efficiency or the operation, the former process is usually advantageous. However, it is advantageous to employ the latter process when the hydrazine starting material is not readily available as a commercial product and it can not easily or economically be produced. Next, the 6-alkoxy-4,5-dihalo-3(2H)pyridazinone derivative of the formula IId-3, can be prepared by reacting the 6-hydroxy derivative of the formula IId-1 or IId-2, with a halogeno derivative of the formula $R_4'$-hal in the presence of a conventional base. Here, a 2-$R_4'$ form (IId-1, $R_1=R_4'$) may be formed as a by-product in addition to the desired O-$R_4'$ form (IId-3, $R_1=H$) in the reaction of the compound IId-2 with $R_4'$-hal. In such a case, good results are often obtained by using a method wherein the reaction is conducted by restricting the ammount of the base to a level of from 1 to 1.2 equivalent, or a method wherein the compound IId-2 is treated with about the same mol of caustic alkali to isolate an alkali In the above formulas, $R_1'$-hal and X are as defined above in Process 1-(2), and $X_1$ is halogen.

Among the benzylamines of the formula III as another starting material in Process I, those hardly available as commercial products, can readily be prepared by the method disclosed in reference (e).

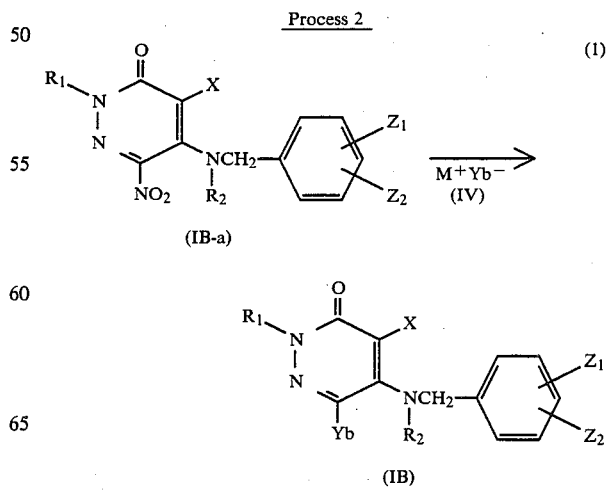

-continued
Process 2

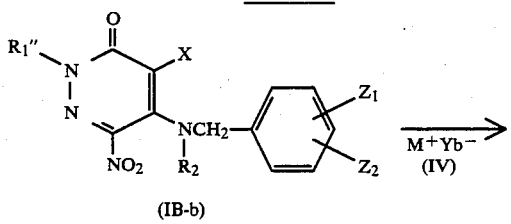
(IB-b)

(IB-c)

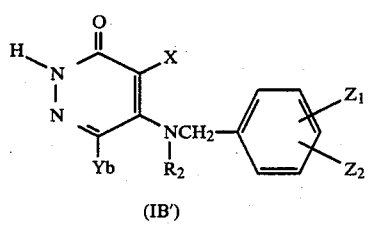
(IB')

In the above formulas, $R_1$, $R_2$, X, $Z_1$ and $Z_2$ are as defined above with respect to the formula I, M is alkali metal, Yb is —NHR or -AR$_4$ wherein $R_3$, A and $R_4$ are as defined above with respect to the formula I, and $R_1''$ is a protective group.

Process 2 comprises a substitution reaction of nitro between a 6-nitro-5-benzylamino derivative of the formula IB-a or IB-b and an alkali metal salt of the formula IV i.e. M$^+$Yb$^-$, to obtain a 6-substituted-5-benzylamino derivative of the formula IB or IB'.

Among the desired compounds, a compound having hydrogen at 2-position of pyridazinone, can be prepared by the direct route as shown in Process 2-(1), or by a route as shown in Process 2-(2) which comprises converting the 6-nitro derivative of the formula IB-b protected at 2-position with $R_1''$ as a starting material to a compound of the formula IB-c and then removing the protective group $R_1''$, to obtain the desired compound.

As the protective group of $R_1''$, 2-trimethylsilylethoxymethyl (Me$_3$Si∨OCH$_2$), methoxymethyl (MeOCH$_2$—) or CO$_2$R wherein R is lower alkyl, is preferably used. The removal of the protective group $R_1''$ can easily be conducted by a conventional method for the removal of such protective groups.

Here, the alkali metal of the formula M includes lithium, sodium and potassium.

Therefore, an alkali metal salt of the formula IV used as a nucleophilic agent in Process 2 includes an alkali metal amide, an alkali metal hydroxide, an alkali metal alkoxide, an alkali metal hydrosulfide and a metal mercaptide.

There is no particular restriction as to the reaction solvent so long as it is inert to the reaction, though it may be suitably selected depending upon the type of the alkali metal salt used for the reaction. For example, in the case of using a metal amide, liquid ammonia or an ether solvent such as diethyl ether, tetrahydrofuran or 1,4-dioxane, is preferably used. In the case of using an alkali metal hydroxide or alkali metal hydrosulfide, good results are often obtained by using an alcohol solvent such as methanol, ethanol, n-propanol or n-butanol, dimethylsulfoxide, an amide solvent such as formamide, N,N-dimethylformamide or N,N-dimethylaceteamide or a polar solvent such as water. In the case of using a metal alkoxide or metal mercaptide, the reaction is usually conducted in the corresponding alcohol or mercaptan. However, the reaction can be conducted in the above-mentioned ether solvent or in a medium including a benzene solvent such as benzene or toluene.

The reaction temperature varies depending upon the reactants used. It is usually within a range of from −78° C. the boiling point of the solvent used for the reaction.

The molar ratio of the starting materials can be optionally determined, and it is sufficient that the alkali metal salt of the formula IV is used in an amount of from 1.2 to 10 mols relative to one mol of the 6-nitro-5-benzylamino derivative of the formula IB-a or IB-b.

The desired compound can readily be isolated and purified by a method known per se in organic syntheses such as recrystallization, various silica gel chromatography or distillation.

Process 3

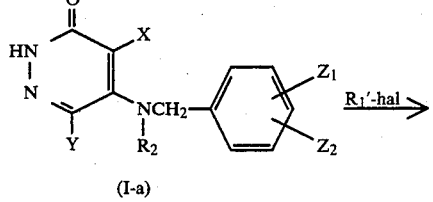
(I-a)

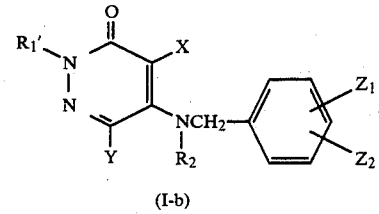
(I-b)

In the above formulas, $R_2$, X, Y, $Z_1$ and $Z_2$ are as defined above with respect to the formula I, and $R_1'$ and hal are as defined above in Process 1-(2).

Process 3 is a process which comprises reacting a compound of the formula I-a i.e. a compound of the formula I having hydrogen at 2-position of pyridazinone, with a halogeno derivative of the formula $R_1'$-hal, to obtain a 2-substituted compound of the formula I-b.

Process 3 is usually conducted in the presence of an inorganic base such as potassium carbonate, sodium carbonate, lithium carbonate, potassium hydrogencarbonate, sodium hydrogencarbonate or lithium hydroxide. Further, in the case where $R_2$ is alkyl in the formula I-a, it is possible to use a metal hydride such as sodium hydride or n-butyl lithium in addition to the above inorganic base.

In the case of using the inorganic base, a ketone solvent such as acetone, methyl ethyl ketone or diethyl ketone, an amide solvent such as formamide, N,N-dimethylformamide or N,N-dimethylaceteamide, an alcohol solvent such as methanol or ethanol, or water, or a mixture thereof, is preferred as the reaction solvent, and in the case of using the metal hydride, an ether solvent is preferably used.

In the case of using the inorganic base, the reaction temperature is usually within a range of from 0° C. to the boiling point of the solvent, and in the case of using the metal hydride, it is usually within a range of from −78° to 60° C.

The molar ratio of the starting materials may optionally be determined. However, the halogen compound of the formula R₁-hal is used usually in an amount of from 1 to 5 mols relative to one mol of the compound of the formula I-a.

The desired compound can be isolated and purified in accordance with the method as described with respect to Process 2.

Process 4

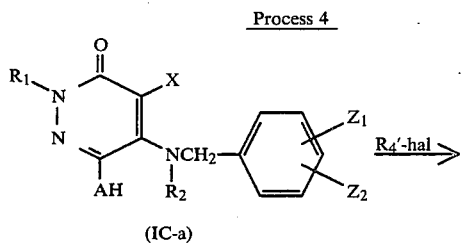

(IC-a)

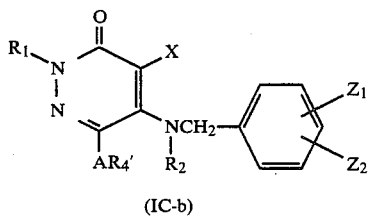

(IC-b)

In the above formulas, R₁, R₂, X, A, Z₁ and Z₂ are as defined above with respect to the formula I, and R₄' and hal are as defined above in Process 1-(2).

Process 4 is a process which comprises reacting a 6-hydroxy or 6-mercapto derivative of the formula IC-a with a halogeno derivative of the formula R₄'-hal, to obtain a 6-alkoxy or 6-substituted mercapto derivative of the formula IC-b.

For Process 4, it is possible to employ the same reaction condition as in the above Process 1-(2) or Process 3.

Process 5

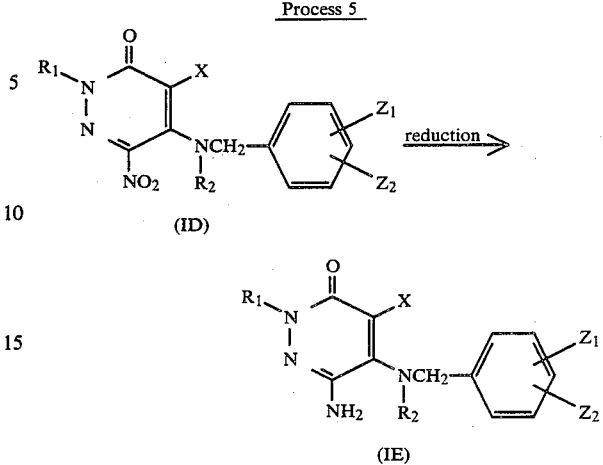

In the above formulas, all symbols are as defined above with respect to the formula I.

Process 5 is a process which comprises a reduction reaction of a 6-nitro derivative of the formula ID, to obtain a 6-amino derivative of the formula IE.

For the reduction, a method of using sodium hydrosulfite, sodium sulfide or the like, or a method of using a metal such as iron, zinc, tin or the like in the presence of acid, may be employed. For this reduction reaction, it is desired to avoid a high temperature or a strong acidic condition with a high concentration of an acid, because a functional group such as halogen or benzyl, in the compound ID, will readily be reduced or eliminated under a strong acidic condition.

A protic solvent such as methanol, ethanol, n-propanol, acetic acid or water, or a mixture thereof, is usually preferably used as the solvent for the reaction. The reaction temperature may be within a range of from −10° to 50° C. In many cases, the reaction proceeds smoothly.

In addition to those described in the Examples given hereinafter, the following compounds (in Table 1) may be mentioned as the compounds of the present invention. In the following compounds, "n" means normal, "i" means iso, "sec" means secondary, "Me" means methyl, "Et" means ethyl, "Pr" means propyl, "Bu" means butyl, "Pen" means pentyl, "Hex" means hexyl, "Hep" means heptyl, "Oct" means octyl, and "Ph" means phenyl.

TABLE 1

| R₁ | R₂ | X | Y | Z₁ | Z₂ |
|---|---|---|---|---|---|
| H | Me | Cl | OEt | 3-OEt | 4-OMe |
| H | Me | Br | OEt | 3-OEt | 4-OMe |
| H | Me | Cl | OEt | 3-O-n-Pr | 4-OMe |
| H | Me | Br | OEt | 3-O-n-Pr | 4-OMe |
| H | Me | Cl | O-i-Pr | 3-OEt | 4-OMe |
| H | Me | Br | O-i-Pr | 3-OEt | 4-OMe |
| H | Me | Cl | O-i-Pr | 3-Cl | 4-OMe |
| H | Me | Br | O-i-Pr | 3-Cl | 4-OMe |
| H | Me | Cl | Cl | 3-OEt | 4-OMe |
| H | Me | Br | Cl | 3-OEt | 4-OMe |

TABLE 1-continued

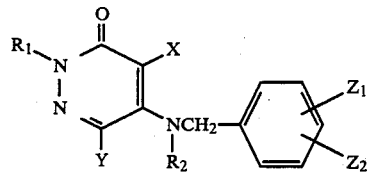

| R₁ | R₂ | X | Y | Z₁ | Z₂ |
|---|---|---|---|---|---|
| H | Me | Cl | OEt | 3-n-Pr | 4-OMe |
| H | Me | Cl | OEt | 3-O-n-Bu | 4-OMe |
| H | Me | Br | OEt | 3-O-n-Bu | 4-OMe |
| H | Me | Cl | OEt | 3-O-n-Pen | 4-OMe |
| H | Me | Br | OEt | 3-O-n-Pen | 4-OMe |
| H | Me | Cl | OEt | 3-O(CH₂)₂Ph | 4-OMe |
| H | Me | Br | OEt | 3-O(CH₂)₂Ph | 4-OMe |
| Et | Me | Cl | OEt | 3-OEt | 4-OMe |
| Et | Me | Br | OEt | 3-OEt | 4-OMe |
| Et | Me | Cl | OEt | 3-O-n-Pr | 4-OMe |
| Et | Me | Br | OEt | 3-O-n-Pr | 4-OMe |
| H | H | Cl | OMe | 3-OMe | 4-OMe |
| H | H | Br | OMe | 3-OEt | 4-OMe |
| H | H | Cl | OMe | 3-O-n-Pr | 4-OMe |
| H | H | Br | OMe | 3-O-n-Pr | 4-OMe |
| H | H | Cl | OMe | 3-O-n-Bu | 4-OMe |
| H | H | Br | OMe | 3-O-n-Bu | 4-OMe |
| H | H | Cl | OMe | H | 4-OEt |
| H | H | Br | OMe | H | 4-OEt |
| H | H | Cl | OMe | H | 4-Et |
| H | H | Br | OMe | H | 4-Et |
| H | H | Cl | OMe | 3-n-Pr | 4-OMe |
| H | H | Br | OMe | 3-n-Pr | 4-OMe |
| H | H | Cl | OMe | 3-OEt | 4-Cl |
| H | H | Br | OMe | 3-OEt | 4-Cl |
| H | H | Cl | SEt | 3-OMe | 4-OMe |
| H | H | Br | OEt | 3-OMe | 4-OMe |
| H | H | Cl | OEt | 2-OMe | 4-OMe |
| H | H | Br | OEt | 2-OMe | 4-OMe |
| H | H | Cl | OEt | 2-Me | 4-Me |
| H | H | Br | OEt | 2-Me | 4-Me |
| H | H | Cl | OEt | 3-Cl | 4-Cl |
| H | H | Br | OEt | 3-Cl | 4-Cl |
| H | H | Cl | OEt | 3-Et | H |
| H | H | Br | OEt | 3-Et | H |
| H | H | Cl | SEt | 3-OEt | 4-OMe |
| H | H | Br | OEt | 3-OEt | 4-OMe |
| H | H | Cl | SEt | 3-O-n-Pr | 4-OMe |
| H | H | Br | OEt | 3-O-n-Pr | 4-OMe |
| H | H | Cl | SEt | 3-O-n-Bu | 4-OMe |
| H | H | Br | OEt | 3-O-n-Bu | 4-OMe |
| H | H | Cl | OEt | 3-O-n-Pen | 4-OMe |
| H | H | Br | OEt | 3-O-n-Pen | 4-OMe |
| H | H | Cl | OEt | 3-O-n-Hex | 4-OMe |
| H | H | Br | OEt | 3-O-n-Hex | 4-OMe |
| H | H | Cl | OEt | 3-O-n-Hep | 4-OMe |
| H | H | Br | OEt | 3-O-n-Hep | 4-OMe |
| H | H | Cl | OEt | 3-O-n-Oct | 4-OMe |
| H | H | Br | OEt | 3-O-n-Oct | 4-OMe |
| H | H | Cl | OEt | 3-O(CH₂)₂Ph | 4-OMe |
| H | H | Br | OEt | 3-O(CH₂)₂Ph | 4-OMe |
| H | H | Cl | OEt | 3-O(CH₂)₃Ph | 4-OMe |
| H | H | Br | OEt | 3-O(CH₂)₃Ph | 4-OMe |
| H | H | Cl | SMe | 3-OMe | 4-OMe |
| H | H | Br | O-i-Pr | 3-OMe | 4-OMe |
| H | H | Cl | O-i-Pr | 2-OMe | 4-OMe |
| H | H | Br | O-i-Pr | 2-OMe | 4-OMe |
| H | H | Cl | O-i-Pr | 2-Me | 4-Me |
| H | H | Br | O-i-Pr | 2-Me | 4-Me |
| H | H | Cl | O-i-Pr | 3-Et | 4-Cl |
| H | H | Cl | O-i-Pr | 3-Et | 4-N(Me)₂ |
| H | H | Cl | O-i-Pr | 3-Cl | 4-Cl |
| H | H | Br | O-i-Pr | 3-Cl | 4-Cl |
| H | H | Cl | O-i-Pr | H | 4-OEt |
| H | H | Br | O-i-Pr | H | 4-OEt |
| H | H | Cl | SMe | 3-OEt | 4-OMe |
| H | H | Br | O-i-Pr | 3-OEt | 4-OMe |
| H | H | Cl | O-i-Pr | 3-OEt | 4-Cl |
| H | H | Br | O-i-Pr | 3-OEt | 4-Cl |
| H | H | Cl | O-i-Pr | 3-OEt | 4-N(Me)₂ |
| H | H | Br | O-i-Pr | 3-OEt | 4-N(Me)₂ |
| H | H | Cl | SMe | 3-O-n-Pr | 4-OMe |

TABLE 1-continued

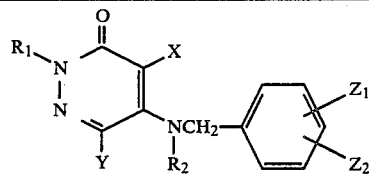

| R₁ | R₂ | X | Y | Z₁ | Z₂ |
|---|---|---|---|---|---|
| H | H | Br | O-i-Pr | 3-O-n-Pr | 4-OMe |
| H | H | Cl | SMe | 3-O-n-Bu | 4-OMe |
| H | H | Br | O-i-Pr | 3-O-n-Bu | 4-OMe |
| H | H | Cl | O-i-Pr | 3-O-n-Pen | 4-OMe |
| H | H | Br | O-i-Pr | 3-O-n-Pen | 4-OMe |
| H | H | Cl | SMe | 3-O-n-Hex | 4-OMe |
| H | H | Br | O-i-Pr | 3-O-n-Hex | 4-OMe |
| H | H | Cl | O-i-Pr | 3-O-n-Hep | 4-OMe |
| H | H | Br | O-i-Pr | 3-O-n-Hep | 4-OMe |
| H | H | Cl | O-i-Pr | 3-O-n-Oct | 4-OMe |
| H | H | Br | O-i-Pr | 3-O-n-Oct | 4-OMe |
| H | H | Cl | O-i-Pr | 3-O(CH₂)₂Ph | 4-OMe |
| H | H | Br | O-i-Pr | 3-O(CH₂)₂Ph | 4-OMe |
| H | H | Cl | Cl | 3-O(CH₂)₂Ph | 4-OMe |
| H | H | Br | Cl | 3-OEt | 4-OMe |
| H | H | Cl | Br | 3-OEt | 4-OMe |
| H | H | Br | Br | 3-OEt | 4-OMe |
| H | H | Cl | F | 3-OEt | 4-OMe |
| H | H | Br | F | 3-OEt | 4-OMe |
| H | H | Cl | NHMe | 3-OEt | 4-OMe |
| H | H | Br | NHMe | 3-OEt | 4-OMe |
| H | H | Cl | NHEt | 3-OEt | 4-OMe |
| H | H | Br | NHEt | 3-OEt | 4-OMe |
| H | H | Cl | Cl | 3-OMe | 4-OMe |
| H | H | Br | Cl | 3-O-n-Pr | 4-OMe |
| H | H | Cl | NHMe | 3-O-n-Pr | 4-OMe |
| H | H | Br | NHMe | 3-O-n-Pr | 4-OMe |
| H | H | Cl | O-n-Pr | 3-OMe | 4-OMe |
| H | H | Br | O-n-Pr | 3-OMe | 4-OMe |
| H | H | Cl | O-i-Bu | 3-OMe | 4-OMe |
| H | H | Br | O-i-Bu | 3-OMe | 4-OMe |
| H | H | Cl | O-n-Pr | 3-OEt | 4-OMe |
| H | H | Br | O-n-Pr | 3-OEt | 4-OMe |
| H | H | Cl | O-i-Bu | 3-OEt | 4-OMe |
| H | H | Br | O-i-Bu | 3-OEt | 4-OMe |
| H | H | Cl | O-n-Pr | 3-O-n-Pr | 4-OMe |
| H | H | Br | O-sec-Bu | 3-OMe | 4-OMe |
| H | H | Br | O-sec-Bu | 3-OEt | 4-OMe |
| H | H | Cl | O-sec-Bu | 3-O-n-Pr | 4-OMe |
| H | H | Br | O-sec-Bu | 3-O-n-Pr | 4-OMe |
| H | H | Cl | O-sec-Bu | 3-O-n-Bu | 4-OMe |
| H | H | Br | O-sec-Bu | 3-O-n-Bu | 4-OMe |
| H | H | Br | O-n-Pr | 3-O-n-Pr | 4-OMe |
| H | H | Cl | O-i-Bu | 3-O-n-Pr | 4-OMe |
| H | H | Br | O-i-Bu | 3-O-n-Pr | 4-OMe |
| H | H | Cl | O-n-Pr | 3-O-n-Bu | 4-OMe |
| H | H | Br | O-n-Pr | 3-O-n-Bu | 4-OMe |
| H | H | Cl | O-i-Bu | 3-O-n-Bu | 4-OMe |
| H | H | Br | O-i-Bu | 3-O-n-Bu | 4-OMe |
| H | H | Cl | O-n-Pr | 3-O(CH₂)₂Ph | 4-OMe |
| Et | H | Br | OMe | 3-O-n-Pr | 4-OMe |
| Et | H | Cl | OEt | 3-OMe | 4-OMe |
| Et | H | Br | OEt | 3-OMe | 4-OMe |
| Et | H | Br | OEt | 3-O-n-Pr | 4-OMe |
| Et | H | Cl | OEt | 3-O-n-Bu | 4-OMe |
| Et | H | Br | OEt | 3-O-n-Bu | 4-OMe |
| i-Pr | H | Cl | OEt | 2-OMe | 4-OMe |
| i-Pr | H | Br | OEt | 2-OMe | 4-OMe |
| i-Pr | H | Cl | OEt | 3-OMe | 4-OMe |
| i-Pr | H | Br | OEt | 3-OMe | 4-OMe |
| i-Pr | H | Cl | OEt | 3-OEt | 4-OMe |
| i-Pr | H | Br | OEt | 3-OEt | 4-OMe |
| i-Pr | H | Cl | OEt | 3-O-n-Bu | 4-OMe |
| i-Pr | H | Br | OEt | 3-O-n-Pr | 4-OMe |
| Et | H | Cl | OEt | 2-Me | 4-Me |
| Et | H | Br | OEt | 2-Me | 4-Me |
| —CH₂CH=CH₂ | H | Cl | OEt | 3-OEt | 4-OMe |
| —CH₂CH=CH₂ | H | Br | OEt | 3-OEt | 4-OMe |
| i-Pr | H | Cl | O-i-Pr | 3-OEt | 4-OMe |
| i-Pr | H | Br | O-i-Pr | 3-OEt | 4-OMe |
| i-Pr | H | Cl | O-i-Pr | 3-O-n-Bu | 4-OMe |
| i-Pr | H | Br | O-i-Pr | 3-O-n-Pr | 4-OMe |

TABLE 1-continued

[Structure: pyridazinone with R1-N-N, X, Y substituents and NCH2-phenyl with Z1, Z2 substituents; N-R2]

| R₁ | R₂ | X | Y | Z₁ | Z₂ |
|---|---|---|---|---|---|
| —CH₂CH=CH₂ | H | Cl | O-i-Pr | 3-OEt | 4-OMe |
| —CH₂CH=CH₂ | H | Br | O-i-Pr | 3-OEt | 4-OMe |
| Me | H | Cl | O-i-Pr | 3-OEt | 4-OMe |
| Me | H | Br | O-i-Pr | 3-OEt | 4-OMe |
| Me | H | Cl | O-i-Pr | 3-O-n-Pr | 4-OMe |
| Me | H | Br | O-i-Pr | 3-O-n-Pr | 4-OMe |
| Et | H | Cl | O-n-Pr | 3-OEt | 4-OMe |
| Et | H | Br | O-n-Pr | 3-OEt | 4-OMe |
| Et | H | Cl | O-n-Pr | 3-OMe | 4-OMe |
| Et | H | Br | O-n-Pr | 3-O-n-Pr | 4-OMe |
| Et | H | Cl | O-i-Bu | 3-OEt | 4-OMe |
| Et | H | Br | O-i-Bu | 3-OEt | 4-OMe |
| Et | H | Cl | Cl | 3-OEt | 4-OMe |
| Et | H | Cl | Br | 3-OEt | 4-OMe |
| Et | H | Br | Cl | 3-OEt | 4-OMe |
| Et | H | Br | Br | 3-OEt | 4-OMe |
| Et | H | Cl | Cl | 3-OMe | 4-OMe |
| Et | H | Br | Cl | 3-O-n-Pr | 4-OMe |
| i-Pr | H | Cl | Cl | 3-OEt | 4-OMe |
| i-Pr | H | Br | Cl | 3-OEt | 4-OMe |
| Et | H | Cl | NHMe | 3-OEt | 4-OMe |
| Et | H | Br | NHMe | 3-OEt | 4-OMe |
| i-Pr | H | Cl | NHMe | 3-OEt | 4-OMe |
| i-Pr | H | Br | NHMe | 3-OEt | 4-OMe |
| Et | H | Cl | NHEt | 3-OEt | 4-OMe |
| Et | H | Br | NHEt | 3-OEt | 4-OMe |
| Et | H | Cl | NHMe | 3-O-n-Pr | 4-OMe |
| Et | H | Br | NHMe | 3-O-n-Pr | 4-OMe |
| H | H | Cl | O-sec-Bu | 3-O(CH₂)₂Ph | 4-OMe |
| H | H | Br | O-sec-Bu | 3-O(CH₂)₂Ph | 4-OMe |
| H | H | Br | OCHMePh | 3-OMe | 4-OMe |
| H | H | Br | OCHMePh | 3-OEt | 4-OMe |
| H | H | Cl | OCHMePh | 3-O-n-Bu | 4-OMe |
| H | H | Br | OCHMePh | 3-O-n-Bu | 4-OMe |
| H | H | Cl | OCHMePh | 3-O(CH₂)₂Ph | 4-OMe |
| H | H | Br | OCHMePh | 3-O(CH₂)₂Ph | 4-OMe |
| H | H | Cl | OCHEtPh | 3-OMe | 4-OMe |
| H | H | Br | OCHEtPh | 3-OMe | 4-OMe |
| H | H | Cl | OCH₂CH=CH₂ | 3-OMe | 4-OMe |
| H | H | Br | OCH₂CH=CH₂ | 3-OMe | 4-OMe |
| H | H | Cl | OCH₂CH=CHMe | 3-OMe | 4-OMe |
| H | H | Br | OCH₂CH=CHMe | 3-OMe | 4-OMe |
| H | H | Cl | OCHMeCH₂CH=CH₂ | 3-OMe | 4-OMe |
| H | H | Br | OCHMeCH₂CH=CH₂ | 3-OMe | 4-OMe |
| H | H | Cl | OCHMeCH₂C≡CH | 3-OMe | 4-OMe |
| H | H | Br | OCHMeCH₂C≡CH | 3-OMe | 4-OMe |

As the manner of administration of the compounds of the present invention, there may be mentioned a non-oral The above pharmacological or veterinary composition contains a compound of the present invention in an amount of from about 0.1 to about 99.5% by weight, preferably from about 0.5 to about 95% by weight, based on the total weight of the composition. To the compound of the present invention or to the composition containing the compound of the present invention, other pharmacologically or veterinarily active compounds may be incorporated. Further, the composition of the present invention may contain a plurality of compounds of the present invention.

The clinical dose of the compound of the present invention varies depending upon the age, the body weight, the sensitivity or the symptom, etc. of the patient. However, the effective daily dose is usually from 0.003 to 1.5 g, preferably from 0.01 to 0.6 g, for an adult. However, if necessary, an amount outside the above range may be employed.

The compounds of the present invention may be formulated into various suitable formulations depending upon the manner of administration, in accordance with conventional methods commonly employed for the preparation of pharmaceutical formulations.

Namely, tablets, capsules, granules or pills for oral administration, may be prepared by using an excipient such as sugar, lactose, glucose, starch or mannitol; a binder such as sirups, gum arabic, gelatin, sorbitol, tragacant gum, methyl cellulose or polyvinylpyrrolidone; a disintegrant such as starch, carboxymethyl cellulose or its calcium salt, crystal cellulose powder or polyethylene glycol; a glass agent such as talc, magnesium or calcium stearate or colloidal silica; or a lubricant such as sodium laurate or glycerol. The injections, solutions, emulsions, suspensions, sirups or aerosols, may be prepared by using a solvent for the active ingredient such as water, ethyl alcohol, isopropyl alcohol, propylene glycol, 1,3-butylene glycol, or polyethylene glycol; a surfactant such as a sorbitol fatty acid ester, a polyoxyethylene sorbitol fatty acid ester, a polyoxyethylene fatty acid ester, a polyoxyethylene ether of hydrogenated caster oil or lecithin; a suspending agent such as a sodium salt of carboxymethyl, a cellulose derivative such as methyl cellulose, or a natural rubber such as tragacant gum or gum arabic; or a preservative such as a paraoxy benzoic acid ester, benzalkonium chloride or a salt of sorbic acid. Likewise, the suppositories may be prepared by using e.g. polyethylene glycol, lanolin or cocoa butter.

TEST EXAMPLES

A. Antagonistic activity test against SRS-A

SRS-A is a mixture of leukotriene $C_4$ (hereinafter referred to as $LTC_4$), leukotriene $D_4$ (hereinafter referred to as $LTD_4$), leukotriene $E_4$ (hereinafter referred to as $LTE_4$) and the like. Accordingly, antagonistic activities against SRS-A can be evaluated by one of the following two test methods:

(1) A method of examining the antagonistic activities against SRS-A obtained from a sensitized guinea-pig, (2) A method of examining the antagonistic activities against $LTC_4$, $LTD_4$ or $LTE_4$.

The present inventors examined the antagonistic activities of compounds of the formula I against SRS-A by using the following test methods.

(1) Test methods
(1) in vitro test $LTD_4$ antagonism in guinea-pig trachea

Antagonism for $LTD_4$ was determined in isolated male guinea-pig (300–400 g) trachea prepared as spiral strip. Tracheal preparations were suspended under 1 g tension in 10 ml organ baths containing 5 μM of indomethacin and they were incubated for 1 hr prior to use. Contractile responses to $LTD_4$ ($2 \times 10^{-8}$ g/ml) were obtained after the maximal response to histamine ($10^{-4}$ M). Test compounds dissolved in 100% dimethyl sulfoxide were added to the organ baths (final concentration of $10^{-6}$ g/ml or $10^{-7}$ g/ml) 30 min prior to $LTD_4$ addition, and then contractile responses to $LTD_4$ were compared with those of control which was obtained from a paired trachea in the absence of test compounds. $LTD_4$-induced contractions were expressed as a percentage of the maximal response to histamine. The antagonism was determined as follows:

Antagonism (%) = (1.0 - % contraction in test/% contraction in control) × 100

FPL-55712 (Fisons Limited) approved as a selective SRS-A antagonist, was used as the control.

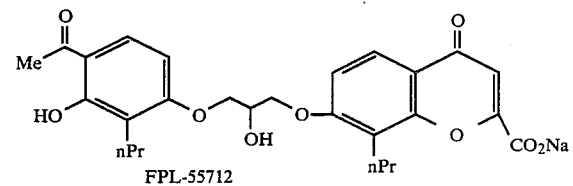

FPL-55712

(2) in vivo test

Effect on anaphylactic bronchoconstriction mediated by endogeneously liberated SRS-A in passively sensitized guinea-pig Male guinea-pigs (350–450 g) were passively sensitized with intravenous (i.v.) injection of 0.125 ml rabbit anti-EA (egg albumin) serum (Capple Laboratories) 1 to 2 days preceding the experiment. Antigen-induced anaphylactic bronchoconstrictions mediated by endogeneously liberated SRS-A were measured by modified method of Konzett and Rossler (Arch. Exp. Path. Pharmak., 195, 71, 1940). Sensitized guinea-pigs were anaesthetized with intraperitoneal injection of urethane (1.5 g/kg). The right jugular vein was cannulated for the administration of the all agents and trachea was cannulated to record total pulmonary resistance. Guinea-pigs were artificially ventilated by a small animal respirator (Shinano, Model SN-480-7) set at a stroke volume of 4.5 ml and a rate of 50 breaths per min. The change in pulmonary resistance was measured with a pressure transducer (Nihon Kohden, Model TP-602T) connected to a T-tube on the tracheal cannula. The increase in air overflow volume was expressed as a percentage of the maximum bronchoconstriction obtained by clamping off the trachea. Following surgical preparation, the animals were pretreated with indomethacin (2 mg/kg, 10 min), pyrilamine (2 mg/kg, 6 min) and propranolol (0.1 mg/kg, 5 min) prior to the EA challenge (0.2 mg/kg). All test compounds were administered orally 2 hrs before the EA challenge. Inhibition (%) of bronchoconstriction was determined as follows: Inhibition (%) = (1.0 - % maximum bronchoconstriction in test/% maximum bronchoconstriction in control) × 100. The maximum bronchoconstriction was 62±6% (Mean±S.E.M; n=6) and the number of test animals was 5–6.

(2) Test Results
(1) in vitro test

LTD$_4$ antagonisms by test compounds at a concentration of $10^{-6}$ g/ml are shown in Table 2. In parenthesis in Table 2, LTD$_4$ antagonisms by test compounds at a concentration of $10^{-7}$ g/ml are shown.

TABLE 2

| Test compound No. | Antagonism (%) | | Test compound No. | Antagonism (%) | |
|---|---|---|---|---|---|
| 5 | 54 | | 64 | 90 | |
| 7 | 50 | | 65 | 96 | |
| 10 | 66 | | 66 | 100 | (48) |
| 22 | 59 | | 67 | 100 | (82) |
| 23 | 51 | | 68 | 92 | |
| 27 | 72 | | 69 | 100 | (83) |
| 30 | 38 | | 70 | 66 | |
| 33 | 93 | | 71 | 66 | |
| 36 | 70 | | 72 | 75 | |
| 45 | 50 | | 73 | 100 | |
| 46 | 73 | | 74 | 100 | |
| 47 | 79 | | 75 | 77 | |
| 48 | 99 | | 77 | 50 | |
| 50 | 95 | | 78 | 56 | |
| 51 | 94 | | 79 | 79 | |
| 52 | 100 | | 80 | 100 | |
| 53 | 100 | | 84 | 59 | |
| 54 | 95 | | 85 | 85 | |
| 55 | 81 | | 86 | 100 | (48) |
| 56 | 100 | (51) | 89 | 96 | (55) |
| 57 | 100 | (37) | 90 | 96 | (70) |
| 58 | 100 | (40) | 91 | 100 | (76) |
| 60 | 100 | (38) | 92 | 63 | |
| 61 | 96 | | 94 | 68 | |
| 63 | 92 | | FPL-55712 | 94 | (48) |

(2) in vivo test

Each of test compounds No. 68 and 69 as representative compounds of the present invention showed significant inhibitory effects over the control at a dose by oral administration as identified in Table 3 (P<0.05). The results are shown in Table 3.

TABLE 3

| Test compound No. | Dose (mg/kg) | Inhibition (%) |
|---|---|---|
| 68 | 30 | 51 |
|  | 10 | 63 |
| 69 | 30 | 52 |

B. Acute toxicity test

The lethal ratio was determined in CD-1(ICR) strain male mice (5 weeks old) at 7 days after the oral administration of test compounds. The results are shown in Table 4.

TABLE 4

| Test compound No. | Dose (mg/kg) | Lethal ratio Death number | Lethal ratio Experimental number |
|---|---|---|---|
| 68 | 1200 | 0 | 5 |
| 69 | 1200 | 0 | 5 |

From these results, it is evident that the compounds of the present invention exhibit prominent antagonistic activities against SRS-A and its major constituents peptide leukotrienes in vitro and in vivo. Further, the compounds of the present invention show strong pharmacological activities and low toxicity even by oral administration. Therefore, the compounds of the present invention are expected to be useful as prophylactic and therapeutic drugs against various immediate type allergic diseases such as bronchial asthma, allergic rhinitics, urticaria and hay fever, various inflamatory diseases such as rheumatoid arthritis and spondyloarthritis, or ischemic heart diseases such as angina pectoris and myocardial infarction, induced by SRS-A or by one of leukotriene C$_4$, D$_4$ and E$_4$ as its constituents or a mixture thereof.

Now, the present invention will be described in detail with reference to Examples including Reference Examples and Formulation Examples. However, it should be understood that the present invention is by no means restricted by these specific Examples. In specific Examples, in Reference Examples, or in Table 5, the symbols "NMR", "IR" and "MS" indicate "nuclear magnetic resonance spectrum", "Infrared spectrum" and "mass spectrometry", respectively. IR was measured by the potassium bromide disk method and NMR was measured in heavy chloroform, unless otherwise specified. In the MS data, only the principal peaks or typical fragment peaks are given.

REFERENCE EXAMPLE 1

2-ethyl-4,5-dichloro-6-hydroxy-3(2H)pyridazinone

A mixture comprising 5.00 g of 3,6-dihydroxy-4,5-dichloropyridazine, 2.21 g of sodium hydroxide, 5.60 g of ethyl iodide, 40 ml of ethanol and water, was stirred at a temperature of from 60° to 70° C. for 4 hours. Most ethanol was distilled off under reduced pressure. Then, dilute hydrochrolic acid and chloroform were added to the residue, and the mixture was vigorously shaken. The chloroform layer was separated and washed with water, followed by drying over sodium sulfate. Then, the solvent was distilled off to obtain a light orange solid substance. The solid substance was treated with benzene to obtain 3.56 g of the above identified compound as colorless crystals.

NMR (CDCl$_3$+DMSO-d$_6$) δ: 4.05(2H, q), 1.33(3H, t).

IR (υmax cm$^{-1}$): 3150, 1635, 1620, 1560, 1510,
MS (m/e): 208(M+), 193, 180(100%), 166, 148.

REFERENCE EXAMPLE 2

4,5-dichloro-6-ethoxy-3(2H)pyridazinone 27.15 g of 3,6-dihydroxy-4,5-dichloropyridazine was dissolved in a solution prepared by dissolving 6.43 g of sodium hydroxide in 200 ml of water, and the solution was subjected to freeze-drying to obtain 32.80 g of sodium salt of 3,6-dihydroxy-4,5-dichloropyridazine as a light yellow powder. A mixture comprising 14.21 g of the sodium salt, 13.10 g of ethyl iodide and 200 ml of N,N-dimethylformamide was stirred at a temperature of from 70° to 80° C. for 4 hours. The solvent was distilled off under reduced pressure, and water was added to the residue thereby obtained. The mixture was extracted with chloroform. The extract was washed with a saturated sodium chloride aqueous solution and dried over sodium sulfate. Then, the solvent was distilled off to obtain a light orange solid substance. The solid substance was washed with 250 ml of a solvent mixture of benzene-ethyl acetate (3:1 v/v) to obtain 2.83 g of the above identified compound having a melting point of from 212° to 212.5° C. as colorless crystals. The residual washing solvent was treated with 10 g of silica gel, and then the solvent was distilled off to obtain a light yellow solid substance. The solid substance was washed with diethyl ether to obtain additional 2.37 g of the above identified compound. (Total yield: 5.20 g)

NMR (CDCl$_3$+DMSO-d$_6$): 4.20(2H, q), 1.38(3H, t).

IR (νmax cm⁻¹): 2975, 2850, 1645, 1585, 1380.
MS (m/e): 208(M+), 180(100%), 150.

In the same manner as above, by using isopropyl iodide, benzyl bromide and α-phenylethyl bromide instead of ethyl iodide, 4,5-dichloro-6-i-propoxy-3(2H)pyridazinone having a melting point of from 210° to 211° C., 4,5-dichloro-6-benzyloxy-3(2H)pyridazinone having a melting point of from 111° to 113° C. and 4,5-dichloro-6 -(α-methylbenzyloxy)-3(2H)pyridazinone having a melting point of from 160° to 161° C. were prepared, respectively.

REFERENCE EXAMPLE 3

2-(2-trimethylsilylethoxymethyl)-4-chloro-5-(3-ethoxy-4-methoxybenzylamino)-6-nitro-3(2H)pyridazinone 587 mg of trimethysilylethoxymethyl chloride was added to a mixture comprising 500 mg of 4-chloro-5-(3-ethoxy-4-methoxybenzylamino)-6-nitro-3(2H)pyridazinone (Compound No. 17), 911 mg of di-i-propylethylamine and 15 ml of dichloromethane, and the mixture was stirred at room temperature for 10 minutes. The solvent was distilled off and the residue thereby obtained was extracted with chloroform. The extract was washed twice with a saturated copper sulfate solution and once with water in this order and dried over sodium sulfate. Then, the solvent was distilled off to obtain a yellow oily substance. The oily substance was purified by silica gel thin layer chromatography by using diethyl ether as the developper, to obtain 600 mg of the above identified compound as a yellow oily substance. This oily substance was allowed to stand to gradually change to crystals having a melting point of from 56° to 57.5° C.

NMR δ: 6.85(3H, s), 6.69(1H, m), 5.48(2H, s), 4.78, 4.68(2H, d), 4.10(2H, q), 3.88(3H, s), 3.80(2H, t), 1.49(3H, t), 1.00(3H, t), 0.0(9H, s).

MS (m/e): 484(M+), 483(100%), 353, 319

In the same manner as above, 2-(2-trimethylsilylethoxymethyl)-4-chloro-5-(3,4-dimethoxybenzylamino)-6-nitro-3(2H)pyridazinone (yellow oily substance) was prepared from 4-chloro-5-(3,4-dimethoxybenzylamino)-6-nitro-3(2H)pyridazinone (Compound No. 87).

REFERENCE EXAMPLE 4

2-(2-trimethylsilylethoxymethy)-4-chloro-5-(3-ethoxy-4-methoxybenzylamino)-6-methoxy-3(2H)pyridazinone A mixture comprising 250 mg of 2-(2-trimethylsilylethoxymethyl)-4-chloro-5-(3-ethoxy-4-methoxybenzylamino)-6-nitro-3(2H)pyridazinone prepared in Reference Example 3, 42 mg of sodium methoxide and methanol, was stirred at room temperature for 10 minutes. Water was added to the reaction mixture and the solvent was distilled off, and the residue thereby obtained was extracted with chloroform. The extract was washed with water and dried over sodium sulfate. Then, the solvent was distilled off to obtain a yellow oily substance. The oily substance was purified by silica gel thin layer chromatography by using diethyl ether as the developer, to obtain 220 mg of the above identified compound as a light yellow oily substance.

NMR δ: 6.78(3H, s), 5.30(2H, s), 5.10(1H, m), 4.82, 4.74(2H, d), 4.10(2H, q), 3.85(6H, s), 3.72(2H, t), 1.48(3H, t), 1.00(3H, t), 0.0(9H, s).

MS (m/e): 469(M+), 468(100%), 304, 188

In the same manner as above, by using sec-butoxide instead of sodium methoxide, 2-(2-trimethylsilylethoxymethy)-4-chloro-5-(3-ethoxy-4-methoxybenzylamino)-6-sec-butoxy-3(2H)pyridazinone (oily substance) and 2-(2-trimethylsilylethoxymethyl)-4-chloro-5-(3,4-dimethoxybenzylamino)-6-sec-butoxy-3(2H)pyridazinone (oily substance), were prepared from the corresponding 2-(2-trimethylsilylethoxymethyl)-4-chloro-5-(3-alkoxy-4-methoxybenzylamino)-6-nitro-3(2H)pyridazinones.

REFERENCE EXAMPLE 5

2-(2-trimethylsilylethoxymethyl)-4-chloro-5-(3,4-dimethoxybenzylamino)-6-n-propylmercapto-3(2H)pyridazinone A solution prepared by dissolving 916 mg of 2-(2-trimethylsilylethoxymethyl)-4-chloro-5-(3,4-dimethoxybenzylamino)-6-nitro-3(2H)pyridazinone prepared in Reference Example 4 in 2 ml of toluene, was dropwise added under cooling with ice and stirring to a mixture comprising of 1 ml of n-propyl mercaptan, 166 mg of sodium amide and 6 ml of toluene. After dropwise addition, the reaction mixture was stirred at the same temperature for further 20 minutes. A saturated ammonium chloride aqueous solution was added to the reaction mixture, and the mixture was extracted with chloroform. The extract was washed with water and dried over sodium sulfate. Then, the solvent was distilled off and the residue thereby obtained was purified by silica gel column chromatography by using benzene-ethyl acetate (12:1 v/v) as the eluent, to obtain 500 mg of the above identified compound as a light yellow oily susbtance.

NMR δ: 6.72(3H, s), 5.33(2H, s), 5.0–4.6(3H, m), 3.81(6H, s), 3.67(2H, t), 2.08(2H, t), 1.9–0.8(7H, m), 0.00(9H, s)

MS (m/e): 499(M+), 456, 398, 383, 164, 151(100%).

In the same manner as above, by using i-propyl mercaptan, i-buthyl mercaptan and sec-buthyl mercaptan instead of n-propyl mercaptan, the respective 6-alkylmercapto forms i.e. 2-(2-trimethylsilylethoxymethyl)-4-chloro-5-(3,4-dimethoxybenzylamino)-6-i-propylmercapto, -6-i-butylmercapto and -6-sec-butylmercapto-3(2H)pyridazinones (each being a light yellow oily substance), were prepared.

EXAMPLE 1

4-bromo-5-(3-n-propoxy-4-methoxy-N-methylbenzylamino)-3(2H)pyridazinone (Compound No. 6)

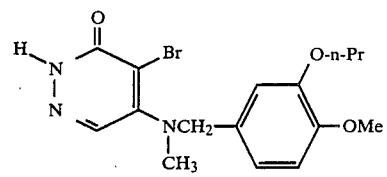

A mixture comprising 300 mg of 4,5-dibromo-3(2H)pyridazinone, 740 mg of 3-n-propoxy-4-methoxy-N-methylbenzylamine and 10 ml of ethanol, was refluxed under stirring for 7 hours. Then, ethanol was distilled off under reduced pressure, dilute hydrochloric acid was added to the residue thereby obtained, and the mixture was extracted with ethyl acetate. The extract was washed twice with water and dried over sodium sulfate. Then, the solvent was distilled off to obtain a yellow solid substance. The product was crystallized from ethyl acetate, to obtain 310 mg of the above identified compound having a melting point of from 149° to 150° C. as light yellow crystals.

NMR δ: 7.53(1H, s), 6.75(3H, s), 4.53(2H, s), 3.91(2H, t), 3.81(3H, s), 3.01(3H, s), 1.84(2H, hexalet), 1.01(3H, t).
MS (m/e): 302(M+-Br,100%), 179, 137.

EXAMPLE 2

4-chloro-5-(3-n-propoxy-4-methoxybenzylamino)-6-nitro-3(2H)pyridazinone (Compound No. 22)

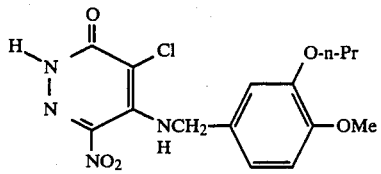

A mixture comprising 8.0 g of 4,5-dichloro-6-nitro-3(2H)pyridazinone, 29.75 g of 3-n-propoxy-4-methoxybenzylamine and 160 ml of ethanol, was refluxed under stirring for 15 hours. Ethanol was distilled off under reduced pressure, and water was added to the residue thereby obtained. The mixture was extracted with chloroform. The extract was washed with water and dried over sodium sulfate. Then, the solvent was distilled off to obtain an orange solid substance. This product was crystallized from a solvent mixture of methanol-water, to obtain 6.50 g of the above identified compound having a melting point of from 169° to 171° C. as orange crystals.

NMR (CDCl₃+DMSO-d₆) δ: 7.01(1H, t), 6.77 (3H, s), 4.62(2H, d), 3.90(2H, t), 3.77(3H, s), 1.78(2H, hexalet), 1.00(3H, t).
MS (m/e): 368(M+), 333, 179(100%), 137.

EXAMPLE 3

4-chloro-5-(3-n-propoxy-4-methoxybenzylamino)-6-amino-3(2H)pyridazinone (Compound No. 23)

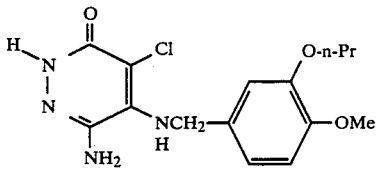

1.00 g of 4-chloro-5-(3-n-propoxy-4-methoxybenzylamino)-6-nitro-3(2H)pyridazinone (Compound No. 22) prepared in Example 2, was dissolved in a solvent mixture of 20 ml of ethanol and 20 ml of a 10% sodium carbonate aqueous solution, 3.30 g of sodium hydrosulfite was gradually added thereto at room temperature under stirring. The mixture was stirred at room temperature for 1 hour, and was neutralized with glacial acetic acid. Then, ethanol was distilled off under reduced pressure, and water was added to the residue thereby obtained. The mixture was extracted with chloroform. The extract was washed with a saturated sodium chloride aqueous solution and dried over sodium sulfate. Then, the solvent was distilled off to obtain light yellow crystals This product was crystallized from a solvent mixture of methanol-diethyl ether, to obtain 634 mg of the above identified compound having a melting point of from 187.5° to 189.5° C. as colorless crystals MS (m/e): 338(M+), 303, 179(100%), 137.

EXAMPLE 4

2-ethyl-4-chloro-5-(3-n-propoxy-4-methoxybenzylamino)-6-nitro-3(2H)pyridazinone (Compound No. 24)

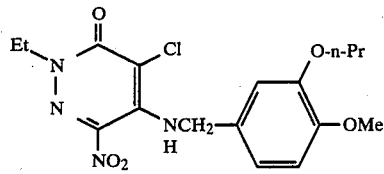

A mixture comprising 500 mg of 4-chloro-5-(3-n-propoxy-4-methoxybenzylamino)-6-nitro-3(2H)pyridazinone (Compound No. 22) prepared in Example 2, 634 mg of ethyl iodide, 562 mg of anhydrous potassium carbonate and 25 ml of methyl ethyl ketone, was refluxed under stirring for 1.5 hours. The solvent was distilled off under reduced pressure, and water was added to the residue thereby obtained and the mixture was extracted with diethyl ether. The extract was washed with a saturated sodium chloride aqueous solution and dried over sodium sulfate. Then, the solvent was distilled off, and the residual oily substance thereby obtained was crystallized from a solvent mixture of diethyl ether-n-hexane, to obtain 473 mg of the above identified compound having a melting point of from 76° to 77° C. as yellow crystals.

NMR δ: 6.79(3H, s), 6.60(1H, broad t), 4.68(2H, d), 4.30(2H, q), 3.93(2H, t), 3.82(3H, s), 1.84(2H, hexalet), 1.39(3H, t), 1.03(3H, t).
MS (m/e): 396(M+), 361, 179(100%), 137.

EXAMPLE 5

2-i-propyl-4-chloro-5-(3-n-propoxy-4-methoxybenzylamino)-6-nitro-3(2H)pyridazinone (Compound No. 25)

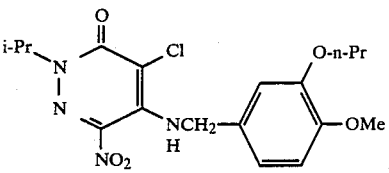

A mixture comprising 500 mg of 4-chloro-5-(3-n-propoxy-4-methoxybenzylamino)-6-nitro-3(2H)pyridazinone (Compound No. 22) prepared in Example 2, 691 mg of isopropyl iodide, 562 mg of anhydrous potassium carbonate and 25 ml of methyl ethyl ketone, was refluxed under stirring for 1.5 hours. The solvent was distilled off under reduced pressure, and water was added to the residue thereby obtained. The mixture was extracted with diethyl ether. The extract was washed with a saturated sodium chloride aqueous solution and dried over sodium sulfate. Then, the solvent was distilled off. The residual oily substance thereby obtained was crystallized from a solvent mixture of diethyl ether-n-hexane, to obtain 435 mg of the above identified compound having a melting point of from 82.5° to 84° C. as yellow crystals.

NMR δ: 6.80(3H, s), 6.63(1H, broad t), 5.25 (1H, heptalet), 4.69(2H, d), 3.94(2H, t), 3.83(3H, s), 1.85(2H, hexalet), 1.38(6H, d), 1.04(3H, t).
MS (m/e): 410(M+), 375, 179(100%), 137.

EXAMPLE 6

2-(2-propenyl)-4-chloro-5-(3-n-propoxy-4-methoxybenzylamino)-6-nitro-3(2H)pyridazinone (Compound No. 26)

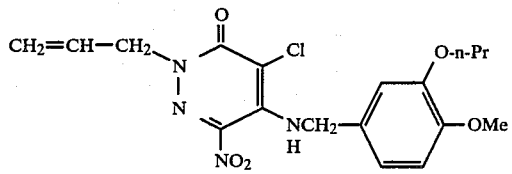

A mixture comprising 500 mg of 4-chloro-5-(3-n-propoxy-4-methoxybenzylamino)-6-nitro-3(2H)pyridazinone (Compound No. 22) prepared in Example 2, 820 mg of allyl bromide, 937 mg of anhydrous potassium carbonate and 25 ml of methyl ethyl ketone, was refluxed under stirring for 1.5 hours. The solvent was distilled off under reduced pressure, water was added to the residue thereby obtained, the mixture was extracted with diethyl ether. The extract was washed with a saturated sodium chloride aqueous solution and dried over sodium sulfate. Then, the solvent was distilled off, and the residue was purified by silica gel column chromatography by using a solvent mixture of benzene: ethyl acetate (85:15 v/v) as the eluent, to obtain 394 mg of the above identified compound having a melting point of from 62.5° to 64° C. as yellow crystals.

NMR δ: 6.81(3H, s), 6.59(1H, broad t), 6.1–4.4(7H, m), 3.95(2H, t), 3.85(3H, s), 1.84(2H, hexalet), 1.02(3H, t).

MS (m/e): 408(M+), 373, 179(100%), 137.

EXAMPLE 7

2-ethyl-4-bromo-5-(3-n-butoxy-4-methoxybenzylamino)-6-amino-3(2H)pyridazinone (Compound No. 32)

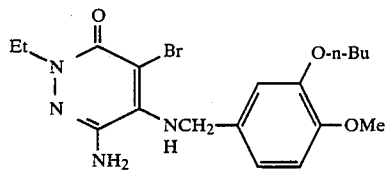

A mixture comprising 280 mg of 4-bromo-5-(3-n-butoxy-4-methoxybenzylamino)-6-amino-3(2H)pyridazinone (Compound No. 30) prepared according to the process of Example 3 from 4-bromo-5-(3-n-butoxy-4-methoxybenzylamino)-6-nitro-3(2H)pyridazinone (Compound No. 29) as the starting material, 0.29 ml of ethyl iodide, 487 mg of anhydrous potassium carbonate and 15 ml of methyl ethyl ketone, was refluxed under stirring for 2 hours. The solvent was distilled off under reduced pressure, and water was added to the residue thereby obtained. The mixture was extracted with chloroform. The extract was washed with a saturated sodium chloride aqueous solution and dried over sodium sulfate. Then, the solvent was distilled off, the residue thereby obtained was subjected to silica gel thin layer chromatography by using a solvent mixture of chloroform:methanol (9:1 v/v) as the developer, the oily substance thereby obtained was crystallized from a solvent mixture of diethyl ether-n-hexane, to obtain 180 mg of the above identified compound having a melting point of from 108° to 110.5° C. as light yellow crystals.

NMR δ: 6.78(3H, s), 5.1–3.8(9H, m), 3.80 (3H, s), 2.0–1.4(4H, m), 1.25, 0.95(each 3H,t).

MS (m/e): 424(M+), 345, 193(100%), 137.

Further, the above identified compound was prepared also by subjecting 2-ethyl-4-bromo-5-(3-n-butoxy-4-methoxybenzylamino)-6-nitro-3(2H)pyridazinone (Compound No. 31) to the same reduction as in Example 3.

EXAMPLE 8

2-ethyl-4-chloro-5-(3-n-propoxy-4-methoxybenzylamino)-6-hydroxy-3(2H)pyridazinone (Compound No. 43)

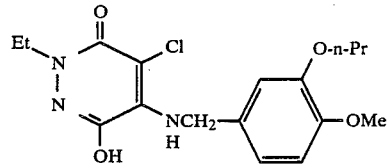

A mixture comprising 523 mg of 2-ethyl-4,5-dichloro-6-hydroxy-3(2H)pyridazinone prepared in Reference Example 1, 1.71 g of 3-n-propoxy-4-methoxybenzylamine, 15 ml of 1,4-dioxane and 15 ml of water, was refluxed under stirring for 24 hours, and 1.71 g of 3-n-propoxy-4-methoxybenzylamine was further added thereto, and the reaction was conducted under the same condition for 2 days. The solvent was distilled off under reduced pressure, and dilute hydrochloric acid was added to the residue thereby obtained. The mixture was extracted with ethyl acetate. The extract was washed with water and a saturated sodium chloride aqueous solution in this order, and dried over sodium sulfate. Then, the solvent was distilled off to obtain a yellow oily substance. The oily substance was purified by silica gel column chromatography, and the slightly yellow oily substance obtained by eluting with a solvent mixture of benzene-ethyl acetate (1:2 v/v) was crystallized from ethyl acetate-diethyl ether, to obtain 418 mg of the above identified compound having a melting point of from 73° to 74° C. as colorless crystals.

NMR δ: 7.79(1H, broad s), 6.79(3H, s), 5.4–5.0(1H, m), 6.9–6.4(2H, m), 3.92(2H, t), 3.81(3H, s), 1.82(2H, hexalet), 1.17, 1.0l(each 3H,t).

MS (m/e): 367(M+), 332, 179(100%), 137.

EXAMPLE 9

2-ethyl-4-chloro-5-(3-n-propoxy-4-methoxybenzylamino)-6-ethoxy-3(2H)pyridazinone (Compound No. 50)

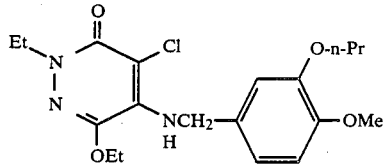

(1) A mixture comprising 184 mg of 2-ethyl-4-chloro-5-(3-n-propoxy-4-methoxybenzylamino)-6-hydroxy-3(2H)pyridazinone (Compound No. 43) prepared in Example 8, 156 mg of ethyl iodide, 207 mg of anhydrous potassium carbonate and 15 ml of methyl ethyl ketone, was refluxed under stirring for 2 hours. The solvent was distilled off under reduced pressure, and water was added to the residue thereby obtained and the mixture was extracted with ethyl acetate. The extract was washed with water and a saturated sodium chloride aqueous solution in this order and dried over sodium sulfate. Then, the solvent was distilled off to obtain a slightly yellow viscous oily substance. The oily substance was crystallized from diethyl ether-n-hexane, to obtain 158 mg of the above identified compound having a melting point of from 77.5° to 78° C. as colorless crystals.

NMR δ: 6.75(3H, s), 5.0–4.6(3H, m), 4.60, 4.40(each 2H, q), 3.93(2H, t), 3.81(3H, s), 1.84(2H, hexalet), 1.35, 1.29, 1.04(each 3H, t).

IR (κmax cm$^{-1}$): 3280, 1625, 1605, 1530. MS (m/e): 395(M+), 360, 179(100%), 137.

(2) 300 mg of 2-ethyl-4-chloro-5-(3-n-propoxy-4-methoxybenzylamino)-6-nitro-3(2H)pyridazinone (Compound No. 24) prepared in Example 4, was dissolved in 6 ml of dried ethanol, and 160 mg of sodium ethoxide was added thereto. The mixture was gently refluxed under stirring for 10 minutes. After cooling, ice water was poured into the reaction solution, and then most ethanol was distilled off under reduced pressure. The residue was extracted with ethyl acetate. The extract was washed with 1N hydrochloric acid, water and a saturated sodium chloride aqueous solution in this order and dried over sodium sulfate. The solvent was distilled off and the residual oily substance thereby obtained was purified by silica gel thin layer chromatography by using benzene:ethyl acetate (7:3 v/v) as the developer, to obtain 300 mg of the above identified compound. The physical properties and the spectrum data of NMR, IR and MS of the compound completely agreed to those of the compound prepared by the above method (1).

EXAMPLE 10

4,6-dichloro-5-(3-n-propoxy-4-methoxybenzylamino)-3(2H)pyridazinone (Compound No. 71)

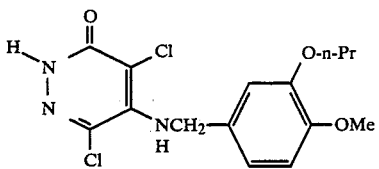

A mixture comprising 997 mg of 4,5,6-trichloro-3(2H)pyridazinone, 3.20 g of 3-n-propoxy-4-methoxybenzylamine and 30 ml of ethanol, was refluxed under stirring for 2 hours. Ethanol was distilled off under reduced pressure, and dilute hydrochloric acid was poured into the residue thereby obtained. The mixture was extracted with ethyl acetate. The extract was washed with water and dried over sodium sulfate. Then, the solvent was distilled off to obtain a light brown viscous oily substance. The residue was subjected to silica gel column chromatography, and the second fraction obtained by eluting with a solvent mixture of benzene-ethyl acetate (2.5:1 v/v) was separated to obtain a colorless solid substance. The product was crystallized from a solvent solution of methanol-diethyl ether, to obtain 513 mg of the above identified compound having a melting point of from 181° to 183° C. as colorless crystals.

NMR (CDCl$_3$+DMSO-d$_6$) δ: 12.72(1H, broad s), 6.79(3H, s), 6.0–5.6(1H, m), 4.78(2H, d), 3.91(2H,t), 3.79(3H, s), 1.80(2H, hexalet), 1.02(3H, t).

MS (m/e): 357(M+), 322, 179(100%), 137.

EXAMPLE 11

2-ethyl-4,6-dichloro-5-(3-n-propoxy-4-methoxybenzylamino)-3(2H)pyridazinone (Compound No. 62)

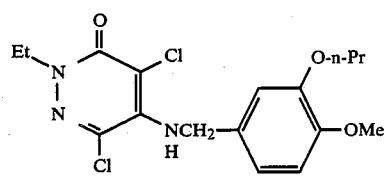

(1) A mixture comprising 150 mg of 4,6-dichloro-5-(3-n-propoxy-4-methoxybenzylamino)-3(2H)pyridazinone (Compound No. 71) prepared in Example 10, 0.2 ml of ethyl iodide, 116 mg of anhydrous potassium carbonate and 10 ml of methyl ethyl ketone, was refluxed under stirring for 1 hour. The reaction mixture was subjected to distillation under reduced pressure, and water was poured into the residue thereby obtained. The mixture was extracted with ethyl acetate. The extract was washed with water and dried over sodium sulfate. Then, the solvent was distilled off to obtain a light yellow viscous oily substance. The product was crystallized from a solvent mixture of diethyl ether-n-hexane, to obtain 139 mg of the above identified compound having a melting point of from 101° to 103° C. as colorless crystals.

NMR δ: 6.83(3H, s), 4.80(3H, broad s), 4.12(2H, q), 3.96(2H, t), 3.84(3H, s), 1.86(2H, hexalet), 1.34, 1.05(each 3H, t).

MS (m/e): 385(M+), 350, 179(100%), 137.

(2) A mixture comprising 455 mg of 2-ethyl-4,5,6-trichloro-3(2H)pyridazinone, 1.20 g of 3-n-propoxy-4-methoxybenzylamine and 20 ml of ethanol, was refluxed under stirring for 3.5 hours. Ethanol was distilled off under reduced pressure, and water was poured into the residue thereby obtained. The mixture was extracted with ethyl acetate. The extract was washed with dilute hydrochloric acid and water in this order and dried over sodium sulfate. Then, the solvent was distilled off to obtain a light brown viscous oily substance. The product was purified by silica gel column chromatography by using a solvent mixture of benzene-ethyl acetate (15:1 v/v) as the eluent, to obtain 277 mg of the above identified compound. The physical properties and the spectrum data of NMR and MS of the compound completely agreed to those of the compound prepared by the method (1).

EXAMPLE 12

4-chloro-5-(3-n-butoxy-4-methoxybenzylamino)-6-ethoxy-3(2H)pyridazinone (Compound No. 68)

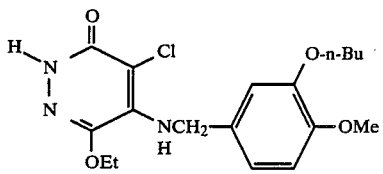

A mixture comprising 7.32 g of 4,5-dichloro-6-ethoxy-3(2H)pyridazinone prepared in Reference Example 2, 21.95 g of 3-n-butoxy-4-methoxybenzylamine, 60 ml of 1,4-dioxane and 60 ml of water, was refluxed under stirring for 15 hours. Then, most 1,4-dioxane was distilled off under reduced pressure, and dilute hydrochloric acid was added for acidification. Then, chloroform was added thereto, and the mixture was vigorously shaked. The precipitated crystals were separated by filtration, and the chloroform layer of the filtrate was subjected to liquid separation and washed with water and dried over sodium sulfate. Then, the solvent was distilled off to obtain a light yellow oily substance. The product was crystallized from n-propanol-di-i-propyl ether (1:9 v/v), to obtain 10.48 g of the above identified compound having a melting point of from 117° to 118° C. as colorless crystals.

NMR δ: 11.79(1H, broad s), 6.76(3H, s), 5.2–4.8 (1H, m), 4.80, 4.71(2H, d), 4.19(2H, q), 3.96(2H, t), 3.81(3H, s), 2.1–1.3(4H, m), 1.32, 0.97(each 3H, t).

MS (m/e): 381(M+), 346, 193(100%), 137.

EXAMPLE 13

4-chloro-5-(3-ethoxy-4-methoxybenzylamino)-6-sec-butoxy-3(2H)pyridazinone (Compound No. 88)

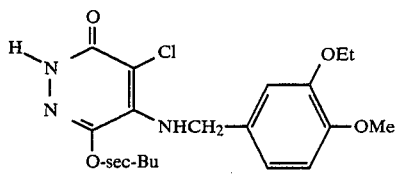

A mixture comprising 150 mg of 2-(2-trimethylsilylethoxymethyl)-4-chloro-5-(3-ethoxy-4-methoxybenzylamino)-6-sec-butoxy-3(2H)pyridazinone prepared in Reference Example 4, 1.46 ml of tetra-n-butylammonium fluoride (1M tetrahydrofuran solution) and 5 ml of 1,2-dimethoxyethane, was refluxed under stirring for 3 hours. The solvent was distilled off under reduced pressure, and the residue thereby obtained was extracted with chloroform. The extract was washed twice with 1N hydrochloric acid and once with water in this order and dried over sodium sulfate. Then, the solvent was distilled off to obtain a dark brown oily substance. The oily substance was purified by silica gel preparative thin layer chromatography by using ethyl acetate as the developer, to obtain a light yellow solid substance. The product was crystallized from chloroform-diethyl ether, to obtain 50 mg of the above identified compound having a melting point of from 130.5° to 132° C. as slightly yellow crystals.

NMR (CDCl$_3$+DMSO-d$_6$) δ: 11.70(1H, s), 6.70(3H, s), 5.02(2H, m), 4.81, 4.74 (2H, d), 4.05(2H, q), 3.82(3H, s), 1.50(9H,m), 1.00(2H, m).

MS (m/e): 381(M+), 346, 165(100%).

EXAMPLE 14

4-chloro-5-(3,4-dimethoxybenzylamino)-6-n-propylmercapto-3(2H)pyridazinone (Compound No. 92)

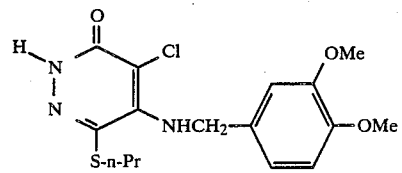

A mixture comprising 256 mg of 2-(2-trimethylsilylethoxymethyl)-4-chloro-5-(3,4-dimethoxybenzylamino)-6-n-propylmercapto-3(2H)pyridazinone prepared in Reference Example 5, 3 ml of tetra-n-butylammonium fluoride (1M tetrahydrofuran solution) and 1.5 ml of N,N-dimethylformamide, was stirred at a temperature of 150° C. for 3 hours. A 1N hydrochloric acid aqueous solution was added to the reaction mixture, and the mixture was extracted with chloroform. The extract was washed with water and a sodium hydrogencarbonate aqueous solution in this order, and dried over sodium sulfate. The solvent was distilled off and the residue thereby obtained was purified by silica gel thin layer chromatography by using benzene-ethyl acetate (1:1 v/v) as the developer, to obtain 39 mg of the above identified compound as a light yellow solid substance. The product was changed into slightly yellow crystals having a melting point of from 129° to 130° C. by the recrystallization thereof from a solvent mixture of ethyl acetate-diethyl ether-n-hexane.

NMR δ: 6.73(3H, s), 5.1–4.4(3H, m), 3.81(6H, s), 2.97(2H, t), 2.1–1.4(2H, m), 0.98(3H, t).

MS (m/e): 369(M+), 334, 165, 151(100%).

The compounds prepared in the same manner as in Examples are shown in Table 5. The Example No. in the right hand side column is the number of the Example in accordance with which the particular compound was prepared.

TABLE 5

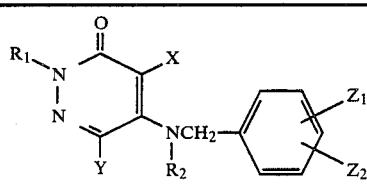

| Compound No. | R$_1$ | R$_2$ | X | Y | Z$_1$ | Z$_2$ | Melting point (°C.) | MS(m/e) | Example No. |
|---|---|---|---|---|---|---|---|---|---|
| 1 | H | Me | Cl | H | 3-OMe | 4-OMe | 169~178 | 309(M+), 151(100%) | 1 |

TABLE 5-continued

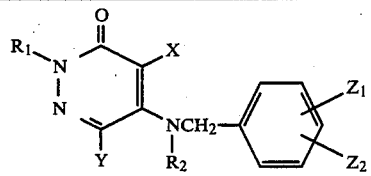

| Compound No. | R₁ | R₂ | X | Y | Z₁ | Z₂ | Melting point (°C.) | MS(m/e) | Example No. |
|---|---|---|---|---|---|---|---|---|---|
| 2 | H | Me | Br | H | 3-OMe | 4-OMe | 160~165.5 | 274(M⁺—Br), 151(100%) | 1 |
| 3 | H | Me | Cl | H | 3-OEt | 4-OMe | 161~162 | 323(M⁺), 165(100%) | 1 |
| 4 | H | Me | Br | H | 3-OEt | 4-OMe | 166~167 | 288(M⁺—Br, 100%), 165 | 1 |
| 5 | H | Me | Cl | H | 3-O-n-Pr | 4-OMe | 144.5~155.5 | 337(M⁺), 179(100%) | 1 |
| 6 | H | Me | Br | H | 3-O-n-Pr | 4-OMe | 149~150 | see Example 1 | 1 |
| 7 | H | Me | Cl | H | 3-O-n-Bu | 4-OMe | 158~159.5 | 351(M⁺), 193(100%) | 1 |
| 8 | H | Me | Br | H | 3-O-n-Bu | 4-OMe | 153~157 | 316(M⁺—Br), 193(100%) | 1 |
| 9 | H | Me | Cl | H | 3-O(CH₂)₂Ph | 4-OMe | 170~173 | 399(M⁺), 241(100%) | 1 |
| 10 | H | Me | Br | H | 3-O(CH₂)₂Ph | 4-OMe | 158~159 | 443(M⁺), 364(100%) | 1 |
| 11 | H | Me | Cl | H | H | 4-Cl | 179~180 | 283(M⁺), 125(100%) | 1 |
| 12 | H | Me | Br | H | H | 4-Cl | 171~173 | 327(M⁺), 248(100%) | 1 |
| 13 | H | Me | Cl | H | 2-Me | 4-Me | 230~235 | 277(M⁺), 119(100%) | 1 |
| 14 | H | Me | Br | H | 2-Me | 4-Me | 210~218 | 242(M⁺—Br), 119(100%) | 1 |
| 15 | H | Et | Cl | H | 3-OEt | 4-OMe | 130~131.5 | 337(M⁺), 165(100%) | 1 |
| 16 | H | Et | Br | H | 3-OEt | 4-OMe | 130~131.5 | 302(M⁺—Br, 100%), 165 | 1 |
| 17 | H | H | Cl | NO₂ | 3-OEt | 4-OMe | 187~188.5 | 354(M⁺), 165(100%) | 2 |
| 18 | H | H | Br | NO₂ | 3-OEt | 4-OMe | 172~174 | 319(M⁺—Br), 165(100%) | 2 |
| 19 | Et | H | Cl | NO₂ | 3-OEt | 4-OMe | 122~123 | 382(M⁺), 165(100%) | 2 |
| 20 | Et | H | Br | NO₂ | 3-OEt | 4-OMe | 122~123 | 426(M⁺), 165(100%) | 2 |
| 21 | Et | Me | Br | NO₂ | 3-OEt | 4-OMe | 97~98 | 440(M⁺), 165(100%) | 2 |
| 22 | H | H | Cl | NO₂ | 3-O-n-Pr | 4-OMe | 169~171 | see Example 2 | 2 |
| 23 | H | H | Cl | NH₂ | 3-O-n-Pr | 4-OMe | 187.5~189.5 | see Example 3 | 3 |
| 24 | Et | H | Cl | NO₂ | 3-O-n-Pr | 4-OMe | 76~77 | see Example 4 | 4 |
| 25 | iPr | H | Cl | NO₂ | 3-O-n-Pr | 4-OMe | 82.5~84 | see Example 5 | 5 |
| 26 | Allyl | H | Cl | NO₂ | 3-O-n-Pr | 4-OMe | 62.5~64 | see Example 6 | 6 |
| 27 | H | H | Br | NO₂ | 3-O-n-Pr | 4-OMe | 165~166.5 | 412(M⁺), 179(100%) | 2 |
| 28 | Et | H | Br | NO₂ | 3-O-n-Pr | 4-OMe | 84~84.5 | 440(M⁺), 179(100%) | 4 |
| 29 | H | H | Br | NO₂ | 3-O-n-Bu | 4-OMe | 130~132 | 426(M⁺), 193(100%) | 2 |
| 30 | H | H | Br | NH₂ | 3-O-n-Bu | 4-OMe | 155~159 | 396(M⁺), 193(100%) | 3 |
| 31 | Et | H | Br | NO₂ | 3-O-n-Bu | 4-OMe | 55~56 | 454(M⁺), 193(100%) | 4 |
| 32 | Et | H | Br | NH₂ | 3-O-n-Bu | 4-OMe | 108~110.5 | see Example 7 | 7,3 |
| 33 | H | H | Br | NO₂ | 3-O-n-Hex | 4-OMe | 138~141 | 454(M⁺), 221(100%) | 2 |
| 34 | H | H | Br | NH₂ | 3-O-n-Hex | 4-OMe | 171~173 | 424(M⁺), 221(100%) | 3 |
| 35 | iPr | H | Br | NO₂ | 3-O-n-Hex | 4-OMe | 57~58.5 | 496(M⁺), 417(100%) | 5 |
| 36 | H | H | Cl | NO₂ | 3-O(CH₂)₂Ph | 4-OMe | 149~150.5 | 430(M⁺), 105(100%) | 2 |
| 37 | H | H | Cl | NH₂ | 3-O(CH₂)₂Ph | 4-OMe | 192~194.5 | 400(M⁺), 241(100%) | 3 |
| 38 | Et | H | Cl | NO₂ | 3-O(CH₂)₂Ph | 4-OMe | oily substance | 458(M⁺), 105(100%) | 4 |
| 39 | H | H | Cl | NO₂ | H | 4-NMe₂ | 147.5~149.5 | 323(M⁺), 134(100%) | 2 |
| 40 | H | H | Cl | NH₂ | H | 4-NMe₂ | 118~123 | 293(M⁺), 134(100%) | 3 |
| 41 | H | Me | Br | NO₂ | H | 4-Cl | 215~219 | 372(M⁺), 125(100%) | 2 |
| 42 | Et | Me | Br | NO₂ | H | 4-Cl | Oily substance | 400(M⁺), 125(100%) | 4 |
| 43 | Et | H | Cl | OH | 3-O-n-Pr | 4-OMe | 73~74 | see Example 8 | 8 |
| 44 | Et | H | Cl | OH | 3-O-n-Bu | 4-OMe | 77~78 | 381(M⁺), 193(100%) | 8 |
| 45 | Et | H | Cl | OMe | 3-OEt | 4-OMe | 103~105 | 367(M⁺), 165(100%) | 9-(ii) |
| 46 | Et | H | Cl | OEt | 3-OEt | 4-OMe | 80.5~81.5 | 381(M⁺), 165(100%) | 9-(ii) |
| 47 | Et | H | Br | OMe | 3-OEt | 4-OMe | 88~89 | 411(M⁺), 332(100%) | 9-(ii) |
| 48 | Et | H | Br | OEt | 3-OEt | 4-OMe | 67.5~69 | 425(M⁺), 346(100%) | 9-(ii) |
| 49 | Et | H | Cl | OMe | 3-O-n-Pr | 4-OMe | 92~93 | 381(M⁺), 179(100%) | 9-(i) |
| 50 | Et | H | Cl | OEt | 3-O-n-Pr | 4-OMe | 77.5~78 | see Example 9 | 9-(i),(ii) |
| 51 | Et | H | Cl | O-i-Pr | 3-OEt | 4-OMe | Oily substance | 395(M⁺), 165(100%) | 9-(ii) |
| 52 | Et | H | Br | O-i-Pr | 3-OEt | 4-OMe | Oily substance | 439(M⁺), 360(100%) | 9-(ii) |
| 53 | Et | H | Cl | O-i-Pr | 3-O-n-Pr | 4-OMe | Oily substance | 409(M⁺), 179(100%) | 9-(ii) |
| 54 | Et | H | Cl | O-CH₂-CH=CH₂ | 3-O-n-Pr | 4-OMe | Oily substance | 407(M⁺), 179(100%) | 9-(ii) |
| 55 | Et | H | Cl | O-CH₂-CH=CH₂ | 3-OEt | 4-OMe | Oily substance | 395(M⁺), 165(100%) | 9-(ii) |
| 56 | Et | H | Br | O-CH₂-CH=CH₂ | 3-OEt | 4-OMe | Oily substance | 439(M⁺), 165(100%) | 9-(ii) |
| 57 | Et | H | Cl | O-n-Pr | 3-O-n-Pr | 4-OMe | Oily substance | 409(M⁺), 179(100%) | 9-(ii) |

TABLE 5-continued

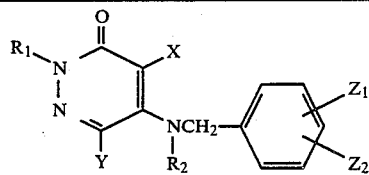

| Compound No. | $R_1$ | $R_2$ | X | Y | $Z_1$ | $Z_2$ | Melting point (°C.) | MS(m/e) | Example No. |
|---|---|---|---|---|---|---|---|---|---|
| 58 | Et | H | Br | O-CH₂-C≡CH | 3-OEt | 4-OMe | 98.5~100 | 435($M^+$), 165(100%) | 9-(ii) |
| 59 | Et | H | Br | O-n-Hex | 3-OEt | 4-OMe | 89~91.5 | 481($M^+$), 165(100%) | 9-(ii) |
| 60 | Et | H | Br | O-CH₂-CH=CH-Me | 3-OEt | 4-OMe | Oily substance | 451($M^+$), 165(100%) | 9-(ii) |
| 61 | Et | H | Br | O-CH₂-C(Me)=CH₂ | 3-OEt | 4-OMe | Oily substance | 451($M^+$), 165(100%) | 9-(ii) |
| 62 | Et | H | Cl | Cl | 3-O-n-Pr | 4-OMe | 101~103 | see Example 11 | 11 |
| 63 | H | H | Cl | O-i-Pr | 3-OMe | 4-OMe | 173~174 | 353($M^+$), 151(100%) | 12 |
| 64 | H | H | Cl | OEt | 3-OEt | 4-OMe | 186.5~188 | 353($M^+$), 165(100%) | 12 |
| 65 | H | H | Cl | O-i-Pr | 3-OEt | 4-OMe | 149.5~150 | 367($M^+$), 165(100%) | 12 |
| 66 | H | H | Cl | OEt | 3-O-n-Pr | 4-OMe | 145~146 | 367($M^+$), 179(100%) | 12 |
| 67 | H | H | Cl | O-i-Pr | 3-O-n-Pr | 4-OMe | 103~104 | 381($M^+$), 179(100%) | 12 |
| 68 | H | H | Cl | OEt | 3-O-n-Bu | 4-OMe | 117~118 | see Example 12 | 12 |
| 69 | H | H | Cl | O-i-Pr | 3-O-n-Bu | 4-OMe | 105~106 | 395($M^+$), 193(100%) | 12 |
| 70 | H | H | Cl | Cl | 3-OEt | 4-OMe | 155~156 | 343($M^+$), 165(100%) | 10 |
| 71 | H | H | Cl | Cl | 3-O-n-Pr | 4-OMe | 181~183 | see Example 10 | 10 |
| 72 | H | H | Cl | O-i-Pr | 3-O-n-Hex | 4-OMe | 84~87 | 423($M^+$), 221(100%) | 10 |
| 73 | Et | Me | Br | OMe | 3-OEt | 4-OMe | Oily substance | 425($M^+$), 346(100%) | 9-(ii) |
| 74 | Et | Me | Br | OEt | 3-OEt | 4-OMe | 81.5~84 | 439($M^+$), 165(100%) | 9-(ii) |
| 75 | Et | H | Cl | OCH₂Ph | 3-O-n-Pr | 4-OMe | Oily substance | 457($M^+$), 366(100%) | 9-(i) |
| 76 | iPr | H | Cl | OMe | 3-O-n-Pr | 4-OMe | 108~110 | 395($M^+$), 179(100%) | 9-(ii) |
| 77 | iPr | H | Cl | OEt | 3-O-n-Pr | 4-OMe | Oily substance | 409($M^+$, 100%) | 9-(ii) |
| 78 | iPr | H | Cl | O-i-Pr | 3-O-n-Pr | 4-OMe | Oily substance | 423($M^+$), 188(100%) | 9-(ii) |
| 79 | iPr | H | Cl | O-CH₂-CH=CH₂ | 3-O-n-Pr | 4-OMe | Oily substance | 421($M^+$, 100%) | 9-(ii) |
| 80 | H | H | Cl | OMe | 3-OEt | 4-OMe | 184~186.5 | 339($M^+$), 165(100%) | 13 |
| 81 | Et | H | Cl | OPh | 3-OEt | 4-OMe | 77~82 | 429($M^+$, 100%) | 9-(ii) |
| 82 | H | H | Cl | O-i-Pr | 2-O-n-Pr | H | 138~144 | 351($M^+$), 149(100%) | 12 |
| 83 | H | H | Cl | O-i-Pr | 2-O-n-Pr | 4-OMe | 126~127.5 | 381($M^+$), 179(100%) | 12 |
| 84 | H | H | Cl | OEt | 3-OMe | 4-OMe | 182~185 | 339($M^+$), 151(100%) | 12 |
| 85 | H | H | Cl | OCH₂Ph | 3-OMe | 4-OMe | 179~180 | 401($M^+$), 91(100%) | 12 |
| 86 | H | H | Cl | OCH₂Ph | 3-OEt | 4-OMe | 182~185 | 415($M^+$), 165(100%) | 12 |
| 87 | H | H | Cl | NO₂ | 3-OMe | 4-OMe | 205~208 | 340($M^+$), 151(100%) | 2 |
| 88 | H | H | Cl | O-sec-Bu | 3-OEt | 4-OMe | 130.5~132 | see Example 13 | 13 |
| 89 | H | H | Cl | O-sec-Bu | 3-OMe | 4-OMe | 151~153 | 367($M^+$), 151(100%) | 13 |
| 90 | H | H | Cl | OCHPh(Me) | 3-OMe | 4-OMe | 126~127 | 415($M^+$), 105(100%) | 12 |
| 91 | H | H | Cl | OCHPh(Me) | 3-OEt | 4-OMe | 95~96 | 429($M^+$), 105(100%) | 12 |
| 92 | H | H | Cl | S-n-Pr | 3-OMe | 4-OMe | 129~130 | see Example 14 | 14 |
| 93 | H | H | Cl | S-i-Pr | 3-OMe | 4-OMe | 179~180 | 369($M^+$), 151(100%) | 14 |
| 94 | H | H | Cl | S-i-Bu | 3-OMe | 4-OMe | 154.5~155 | 383($M^+$), 151(100%) | 14 |
| 95 | H | H | Cl | O-sec-Bu | 3-OMe | 4-OMe | 169~170 | 383($M^+$), 151(100%) | 14 |

Now, Formulation Examples of the compounds of the formula I will be given.

FORMULATION EXAMPLES 1 and 2 (Tablets)

| | |
|---|---|
| Compound No. 53 (Formulation Example 1) or Compound No. 68 (Formulation Example 2) | 10 g |
| -continued | |
| Lactose | 20 g |
| Starch | 4 g |
| Starch for paste | 1 g |
| Magnesium stearate | 100 mg |
| Carboxymethyl cellulose calcium | 7 g |

-continued

| | |
|---|---|
| Total | 42 1 g |

The above components were mixed in a usual manner, and formulated into sugar-coated tablets each containing 50 mg of an active ingredient.

| FORMULATION EXAMPLES 3 and 4 (Capsules) | |
|---|---|
| Compound No. 52 (Formulation Example 3) or Compound No. 69 (Formulation Example 4) | 10 g |
| Lactose | 20 g |
| Crystal cellulose powder | 10 g |
| Magnesium stearate | 1 g |
| Total | 41 g |

The above components were mixed in a usual manner, and filled into gelatin capsules to obtain capsules each containing 50 mg of an active ingredient.

| FORMULATION EXAMPLES 5 and 6 (Soft capsules) | |
|---|---|
| Compound No. 48 (Formulation Example 5) or Compound No. 91 (Formulation Example 6) | 10 g |
| Corn Oil | 35 g |
| Total | 45 g |

The above components were mixed and formulated in a usual manner to obtain soft capsules.

| FORMULATION EXAMPLES 7 and 8 (Ointment) | |
|---|---|
| Compound No. 51 (Formulation Example 7) or Compound No. 89 (Formulation Example 8) | 1.0 g |
| Olive Oil | 20 g |
| White vaseline | 79 g |
| Total | 100 g |

The above components were mixed in a usual manner to obtain 1% ointment.

| FORMUALTION EXAMPLES 9 and 10 (Aerosol suspension) | | |
|---|---|---|
| (A) | Compound No. 33 (Formulation Example 9) or Compound No. 67 (Formulation Example 10) | 0.25(%) |
| | Isopropyl myristate | 0.10 |
| | Ethanol | 26.40 |
| (B) | A 60–40% mixture of 1,2-dichlorotetrafluoroethane and 1-chloropentafluoroethane | 73.25 73.25 |

The above composition (A) was mixed. The solution mixture thereby obtained was charged in a container equipped with a valve, and the propellant (B) was injected from a valve nozzle to a gauge pressure of from about 2.46 to 2.81 mg/cm² to obtain an aerosol suspension.

We claim:

1. A 3(2H)pyridazinone of the formula:

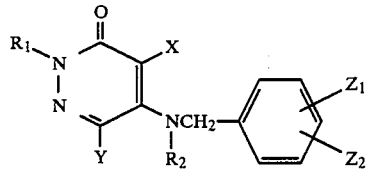

(I)

wherein $R_1$ is hydrogen, 2-propenyl or straight chained or branched $C_1$–$C_4$ alkyl; $R_2$ is hydrogen or $C_1$–$C_3$ alkyl; X is chlorine or bromine; Y is nitro, —$NHR_3$ wherein $R_3$ is hydrogen or straight chained or branched $C_1$–$C_4$ alkyl, —$AR_4$ wherein A is oxygen or sulfur and $R_4$ is hydrogen, straight chained or branched $C_1$–$C_6$ alkyl, $C_3$–$C_6$ alkenyl having one double bond, $C_3$–$C_6$ alkynyl having one triple bond, phenyl or

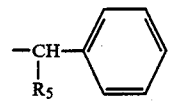

wherein $R_5$ is hydrogen or $C_1$–$C_4$ alkyl, or halogen; $Z_1$ is hydrogen, $C_1$–$C_4$ alkyl, —$OR_6$ wherein $R_6$ is hydrogen, straight chained or branched $C_1$–$C_8$ alkyl or

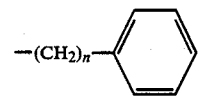

wherein n is an interger of from 1 to 4, —$N(R_7)_2$ wherein $R_7$ is $C_1$–$C_4$ alkyl, or halogen; $Z_2$ is $C_1$–$C_4$ alkyl, —$OR_6$ wherein $R_6$ is as defined above, —$N(R_7)_2$ wherein $R_7$ is as defined above, or halogen, provided that when $R_1$ is straight chained or branched $C_2$–$C_4$ alkyl, Y is not hydrogen and when $R_1$ is hydrogen, methyl or 2-propenyl, Y and $R_2$ are not simultaneously hydrogen, or a pharmaceutically acceptable salt thereof.

2. The compound according to claim 1, wherein $Z_2$ is —$OR_6$ wherein $R_6$ is as defined above, —$N(R_7)_2$ wherein $R_7$ is as defined above, or halogen.

3. The compound according to claim 2, wherein $R_2$ is hydrogen.

4. The compound according to claim 3, wherein $R_1$ is hydrogen, 2-propenyl, ethyl or isopropyl.

5. The compound according to claim 4, wherein Y is nitro, amino, —$AR_4$ wherein A and $R_4$ are as defined above, or halogen.

6. The compound according to claim 5, wherein halogen is chlorine.

7. The compound according to claim 6, wherein $Z_1$ is hydrogen, $C_1$–$C_4$ alkyl, —$OR_6$ wherein $R_6$ is as defined above, —$N(CH_3)_2$ or chlorine, and $Z_2$ is —$OR_6$ wherein $R_6$ is as defined above, —$N(CH_3)_2$ or chlorine.

8. The compound according to claim 7, wherein $R_1$ is hydrogen, ethyl or isopropyl.

9. The compound according to claim 8, wherein $Z_1$ is hydrogen or —$OR_6$ wherein $R_6$ is straight chained $C_1$–$C_8$ alkyl or

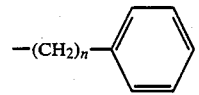

wherein n is as defined above, and $Z_2$ is —$OR_6$ wherein $R_6$ is straight chained $C_1$–$C_8$ alkyl or

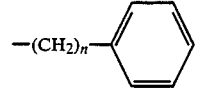

wherein n is defined above.

10. The compound according to claim 9, wherein Y is —OR$_4$ wherein R$_4$ is straight chained or branched C$_1$–C$_6$ alkyl, C$_3$–C$_6$ alkenyl having one double bond, C$_3$–C$_6$ alkynyl having one triple bond, phenyl or

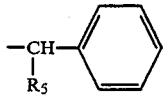

wherein R$_5$ is as defined above.

11. The compound according to claim 10, wherein R$_1$ is hydrogen.

12. The compound according to claim 11, wherein each of Z$_1$ and Z$_2$ which may be the same or different is —OR$_6$ wherein R$_6$ is straight chained C$_1$–C$_6$ alkyl or

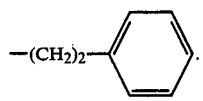

13. The compound according to claim 12, wherein Y is —OR$_4$ wherein R$_4$ is straight chained or branched C$_1$–C$_6$ alkyl, —CH$_2$C(R$_4'$)=C(R$_4''$)(R$_4'''$) wherein each of R$_4'$, R$_4''$ and R$_4'''$ which may be the same or different is hydrogen or methyl, —CH$_2$C≡C—R$_4'$ wherein R$_4'$ is as defined above, phenyl or

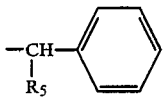

wherein R$_5$ is hydrogen or C$_1$–C$_4$ alkyl.

14. The compound according to claim 13, wherein Z$_1$ is 3-OR$_6$ wherein R$_6$ is straight chained C$_1$–C$_6$ alkyl or

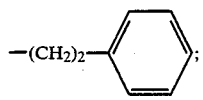

and Z$_2$ is 4-OCH$_3$.

15. The compound according to claim 14, wherein Y is —OR$_4$ wherein R$_4$ is straight chained or branched C$_1$–C$_6$ alkyl, 2-propenyl, propargyl methyl, phenyl or

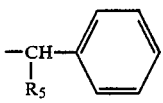

wherein R$_5$ is hydrogen or methyl.

16. The compound according to claim 15, wherein X is chlorine.

17. The compound according to claim 16, wherein Y is —OR$_4$ wherein R$_4$ is straight chained or branched C$_1$–C$_4$ alkyl or

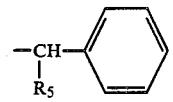

wherein R$_5$ is hydrogen or methyl.

18. An antagonistic agent against SRS-A comprising an effective amount of a 3(2H)pyridazinone of the formula I as defined in claim 1 or a pharmaceutically acceptable salt thereof and a pharmaceutically acceptable carrier.

19. A method of reducing the incidence or severity of allergy induced in a subject by SRS-A, which comprises administering to said subject an amount effective to reduce the incidence or severity of the allergy of a 3(2H)pyridazinone as defined in claim 1 or a pharmaceutically acceptable salt thereof.

20. The compound according to claim 1, which is 4-chloro-5-(3-n-butoxy-4-methoxybenzylamino-6-ethoxy-3(2H)pyridazinone.

21. The compound according to claim 1, which is 4-bromo-5-(3-n-butoxy-4-methoxybenzylamino)-6-ethoxy-3(2H)pyridazinone.

22. The compound according to claim 1, which is 4-chloro-5-(3-i-butoxy-4-methoxybenzylamino)-6-ethoxy-3(2H)pyridazinone.

23. The compound according to claim 1, which is 4-bromo-5-(3-i-butoxy-4-methoxybenzylamino)-6-ethoxy-3(2H)pyridazinone.

24. The compound according to claim 1, which is 4-chloro-5-(3-i-butoxy-4-methoxybenzylamino)-6-i-propoxy-3(2H)pyridazinone.

25. The compound according to claim 1, which is 4-bromo-5-(3-i-butoxy-4-methoxybenzylamino)-6-i-propoxy-3(2H)pyridazinone.

26. The compound according to claim 1, which is 4-chloro-5-(3-i-butoxy-4-methoxybenzylamino)-6-n-propoxy-3(2H)pyridazinone.

27. The compound according to claim 1, which is 4-chloro-5-(3-i-butoxy-4-methoxybenzylamino)-6-α-methylbenzyloxy-3(2H)pyridazinone.

28. The compound according to claim 1, which is 4-bromo-5-(3,4-dimethoxybenzylamino)-6-i-propoxy-3(2H)pyridazinone.

29. The compound according to claim 1, which is 4-chloro-5-(3-n-butoxy-4-methoxybenzylamino)-6-i-propoxy-3(2H)pyridazinone, 4-bromo-5-(3-n-butoxy-4-methoxybenzylamino)-6-i-propoxy-3(2H)pyridazinone, 4-chloro-5-(3-n-butoxy-4-methoxybenzylamino)-6-n-propoxy-3(2H)pyridazinone, 4-bromo-5-(3-n-butoxy-4-methoxybenzylamino)-6-n-propoxy-3(2H)pyridazinone, 4-bromo-5-(3-i-butoxy-4-methoxybenzylamino)-6-n-propoxy-3(2H)pyridazinone, 4-chloro-5-(3-n-butoxy-4-methoxybenzylamino)-6-sec-butoxy-3(2H)pyridazinone, 4-bromo-5-(3-n-butoxy-4-methoxybenzylamino)-6-sec-butoxy-3(2H)pyridazinone, 4-chloro-5-(3-n-butoxy-4-methoxybenzylamino)-6-benzyloxy-3(2H)pyridazinone, 4-bromo-5-(3-n-butoxy-4-methoxybenzylamino)-6-benzyloxy-3(2H)pyridazinone, 4-chloro-5-(3-n-butoxy-4-methoxybenzylamino)-6-α-methylbenzyloxy-3(2H)pyridazinone, 4-bromo-5-(3-n-butoxy-4-methoxybenzylamino)-6-α-methylbenzyloxy-3(2H)pyridazinone, 4-bromo-5-(3-i-butoxy-4-methoxybenzylamino)-6-α-methylbenzyloxy-3(2H)pyridazinone, 4-chloro-5-(3-n-propoxy-4-methoxybenzylamino)-6-ethoxy-3(2H)pyridazinone, 4-bromo-5-(3- n-propoxy-4-methoxybenzylamino)-6-ethoxy-3(2H)pyridazinone, 4-chloro-5-(3-n-propoxy-4-methoxybenzylamino)-6-i-propoxy-3(2H)pyridazinone, 4-bromo-5-(3-n-propoxy-4-methoxybenzylamino)-6-i-propoxy-3(2H)pyridazinone, 4-chloro-5-(3-n-propoxy-4-methoxybenzylamino)-6-α-methoxybenzyloxy-3(2H)pyridazinone, 4-bromo-5-(3-n-propoxy-4-methoxybenzylamino)-6-α-methoxybenzyloxy-3(2H)pyridazinone, 4-chloro-5-(3-ethoxy-4-methoxybenzylamino)-6-ethoxy-3(2H)pyridazinone, 4-bromo-5-(3-ethoxy-4-methoxybenzylamino)-6-ethoxy-3(2H)pyridazinone, 4-chloro-5-(3-ethoxy-4-methoxybenzylamino)-6-i-propoxy-3(2H)pyridazinone, 4-bromo-5-(3-ethoxy-4-methoxybenzylamino)-6-i-propoxy-3(2H)pyridazinone, 4-chloro-5-(3-ethoxy-4-methoxybenzylamino)-6-α-methylbenzyloxy-3(2H)pyridazinone, 4-bromo-5-(3-ethoxy-4-methoxybenzylamino)-6-α-methylbenzyloxy-3(2H)pyridazinone, 4-chloro-5-(3-ethoxy-4-methoxybenzylamino)-6-sec-butoxy-3(2H)pyridazinone, 4-bromo-5-(3-ethoxy-4-methoxybenzylamino)-6-sec-butoxy-3(2H)pyridazinone, 4-chloro-5-(3,4-dimethoxybenzylamino)-6-ethoxy-3(2H)pyridazinone, 4-bromo-5-(3,4-dimethoxybenzylamino)-6-ethoxy-3(2H)pyridazinone, 4-chloro-5-(3,4-dimethoxybenzylamino)-6-i-propoxy-3(2H)pyridazinone, 4-chloro-5-(3,4-dimethoxybenzylamino)-6-α-methylbenzyloxy-3(2H)pyridazinone, 4-bromo-5-(3,4-dimethoxybenzylamino)-6-α-methylbenzyloxy-3(2H)pyridazinone, 4-chloro-5-(3,4-dimethoxybenzylamino)-6-sec-butoxy-3(2H)pyridazinone, 4-bromo-5-(3,4-dimethoxybenzylamino)-6-sec-butoxy-3(2H)pyridazinone, 4-chloro-5-{3-(2-phenylethoxy)-4-methoxybenzylamino}-6-ethoxy-3(2H)pyridazinone, 4-bromo-5-{3-(2-phenylethoxy)-4-methoxybenzylamino}-6-ethoxy-3(2H)pyridazinone, 4-chloro-5-{3-(2-phenylethoxy)-4-methoxybenzylamino}-6-i-propoxy-3(2H)pyridazinone, 4-bromo-5-{3-(2-phenylethoxy)-4-methoxybenzylamino}-6-ethoxy-3(2H)pyridazinone, 4-chloro-5-{3-(2-phenylethoxy)-4-methoxybenzylamino}-6-i-propoxy-3(2H)pyridazinone, 4-bromo-5-{3-(2-phenylethoxy)-4-methoxybenzylamino}-6-i-propoxy-3(2H)pyridazinone, 4-chloro-5-(3-n-pentyloxy-4-methoxybenzylamino)-6-i-propoxy-3(2H)pyridazinone, 4-bromo-5-(3-n-pentyloxy-4-methoxybenzylamino)-6-i-propoxy-3(2H)pyridazinone, 4-chloro-5-(3-n-hexyloxy-4-methoxybenzylamino)-6-i-propoxy-3(2H)pyridazinone, 4-chloro-5-(3-i-pentyloxy-4-methoxybenzylamino)-6-i-propoxy-3(2H)pyridazinone, 4-chloro-5-(3-sec-butoxy-4-methoxybenzylamino)-6-i-propoxy-3(2H)pyridazinone, or 4-chloro-5-(3-sec-pentyloxy-4-methoxybenzylamino)-6-i-propoxy-3(2H)pyridazinone.

* * * * *

UNITED STATES PATENT AND TRADEMARK OFFICE
CERTIFICATE OF CORRECTION

PATENT NO. : 4,978,665
DATED : DECEMBER 18, 1990
INVENTOR(S) : KEIZO TANIKAWA ET AL

It is certified that error appears in the above-identified patent and that said Letters Patent is hereby corrected as shown below:

Column 1, line 16, change "leukotriene" to --leukotrienes--.

line 58, change "3(2)" to --3(2H)--.

Column 6, line 51, change "No. 5298/1969" to --No. 5398/1969--.

Column 9, line 49, change "$Me_3Si\vee OCH_2$" to --$Me_3Si\wedge OCH_2$--.

Column 10, line 14, change "C the" to --C. to the--.

Signed and Sealed this

Twenty-ninth Day of December, 1992

*Attest:*

DOUGLAS B. COMER

*Attesting Officer*      *Acting Commissioner of Patents and Trademarks*